United States Patent
De Almeida Barreto et al.

(10) Patent No.: US 12,220,104 B2
(45) Date of Patent: Feb. 11, 2025

(54) SYSTEMS AND METHODS FOR CHANGING THE DIRECTION OF VIEW DURING VIDEO GUIDED CLINICAL PROCEDURES USING REAL-TIME IMAGE PROCESSING

(71) Applicant: S&N Orion Prime, S.A., Austin, TX (US)

(72) Inventors: João Pedro De Almeida Barreto, Coimbra (PT); Carolina Dos Santos Raposo, Coimbra (PT); Michel Goncalves Almeida Antunes, Coimbra (PT); Rui Jorge Melo Teixeira, Tondela (PT)

(73) Assignee: S&N Orion Prime, S.A., Austin, TX (US)

( * ) Notice: Subject to any disclaimer, the term of this patent is extended or adjusted under 35 U.S.C. 154(b) by 515 days.

(21) Appl. No.: 17/762,205

(22) PCT Filed: Oct. 7, 2020

(86) PCT No.: PCT/US2020/054640
§ 371 (c)(1),
(2) Date: Mar. 21, 2022

(87) PCT Pub. No.: WO2021/071991
PCT Pub. Date: Apr. 15, 2021

(65) Prior Publication Data
US 2022/0383588 A1 Dec. 1, 2022

Related U.S. Application Data

(60) Provisional application No. 62/911,986, filed on Oct. 7, 2019, provisional application No. 62/911,950, filed on Oct. 7, 2019.

(51) Int. Cl.
*A61B 1/00* (2006.01)
*G06T 3/18* (2024.01)
(Continued)

(52) U.S. Cl.
CPC ...... *A61B 1/00179* (2013.01); *A61B 1/00009* (2013.01); *A61B 1/000094* (2022.02);
(Continued)

(58) Field of Classification Search
None
See application file for complete search history.

(56) References Cited

U.S. PATENT DOCUMENTS

| 5,313,306 A | 5/1994 | Kuban et al. |
| 7,344,494 B2 | 3/2008 | Hoeg et al. |

(Continued)

FOREIGN PATENT DOCUMENTS

| EP | 3 130 276 B1 | 1/2020 |
| WO | 2021071988 A1 | 4/2021 |

(Continued)

OTHER PUBLICATIONS

International Patent Application No. PCT/US2022/041845 filed Aug. 29, 2022 listing Quist, Brian William as first inventor, entitled, "Methods and Systems of Ligament Repair," 108 pages.
(Continued)

*Primary Examiner* — Samira Monshi
(74) *Attorney, Agent, or Firm* — Dickinson Wright PLLC

(57) ABSTRACT

Arthroscopes and laparoscopes are available in several lens cuts to cover different clinical situations of interest, with the surgeon having to exchange the optics in order to change the direction of view of the camera. The presently disclosed embodiments disclose real-time image processing systems and methods that enable the user to arbitrarily change the direction of view of a surgical camera with the advantage of avoiding the disruption in workflow caused by the physical exchange of the optics. In addition, the presently disclosed embodiments disclose performing zoom along an arbitrary viewing direction (directional zoom) that enables to increase (Continued)

the scale of a region of interest without decreasing the overall field-of-view or losing image contents.

30 Claims, 13 Drawing Sheets

(51) Int. Cl.
*G06T 7/13* (2017.01)
*G06T 7/33* (2017.01)
*G06T 7/80* (2017.01)
*G06T 15/20* (2011.01)

(52) U.S. Cl.
CPC .......... *A61B 1/000096* (2022.02); *G06T 3/18* (2024.01); *G06T 7/13* (2017.01); *G06T 7/33* (2017.01); *G06T 7/80* (2017.01); *G06T 15/205* (2013.01); *G06T 2207/10* (2013.01); *G06T 2207/10068* (2013.01); *G06T 2210/41* (2013.01)

(56) References Cited

U.S. PATENT DOCUMENTS

| | | |
|---|---|---|
| 8,444,652 B2 | 5/2013 | Amis et al. |
| 8,852,086 B2 | 10/2014 | Pauli et al. |
| 8,864,652 B2 | 10/2014 | Diolaiti et al. |
| 9,307,892 B2 | 4/2016 | Dahmen |
| 9,438,897 B2 | 9/2016 | De Almeida Baretto et al. |
| 9,516,996 B2 | 12/2016 | Diolaiti et al. |
| 9,591,962 B2 | 3/2017 | Hoeg et al. |
| 10,092,169 B2 | 10/2018 | Hale et al. |
| 10,134,133 B2 | 11/2018 | Zhao et al. |
| 10,307,296 B2 | 6/2019 | Tan et al. |
| 10,499,996 B2 | 12/2019 | de Almeida Barreto |
| 11,252,395 B2 | 2/2022 | Zhao et al. |
| 2005/0177026 A1 | 8/2005 | Hoeg et al. |
| 2007/0236514 A1 | 10/2007 | Agusanto et al. |
| 2008/0021282 A1 | 1/2008 | Hoeg et al. |
| 2009/0326556 A1 | 12/2009 | Diolaiti et al. |
| 2010/0245541 A1 | 9/2010 | Zhao et al. |
| 2012/0078049 A1 | 3/2012 | Pauli et al. |
| 2012/0268579 A1 | 10/2012 | Zhao et al. |
| 2014/0142385 A1 | 5/2014 | Dahmen |
| 2014/0285676 A1 | 9/2014 | De Almeida Baretto et al. |
| 2015/0065793 A1 | 3/2015 | Diolaiti et al. |
| 2015/0065799 A1 | 3/2015 | Hale et al. |
| 2015/0351967 A1 | 12/2015 | Lim et al. |
| 2016/0048953 A1 | 2/2016 | Zhao et al. |
| 2016/0220099 A1 | 8/2016 | Schouwink et al. |
| 2020/0228783 A1 | 7/2020 | Zhao et al. |
| 2021/0161718 A1 | 6/2021 | Ng et al. |
| 2021/0204802 A1 | 7/2021 | Nir et al. |

FOREIGN PATENT DOCUMENTS

| | | |
|---|---|---|
| WO | 2021168408 A1 | 8/2021 |
| WO | 2021203077 A1 | 10/2021 |
| WO | 2021203082 A1 | 10/2021 |
| WO | 2021257672 A1 | 12/2021 |
| WO | 2022006041 A1 | 1/2022 |
| WO | 2022006248 A1 | 1/2022 |
| WO | 2022159726 A1 | 7/2022 |

OTHER PUBLICATIONS

International Patent Application No. PCT/US2022/046857 filed Oct. 17, 2022 listing Torrie, Paul Alexander as first inventor, entitled, "Methods and Systems of Tracking Objects in Medical Procedures," 77 pages.

Japanese Application No. 2022-520932, Notice of Reasons for Rejection.

International Search Report and Written Opinion of PCT/US2020/054640 mailed Jan. 6, 2021.

$$\mathbf{u}_s = w(\mathbf{u}_t) = c_s \circ m \circ c_t^{-1}(\mathbf{u}_t)$$

Source image
(lens cut $\beta$, FOV $\Theta$)

Target image
(lens cut $\hat{\beta}_1$, FOV $\hat{\Theta}_1$)

Target image
(lens cut $\hat{\beta}_2$, FOV $\hat{\Theta}_2$)

SYSTEMS AND METHODS FOR CHANGING THE DIRECTION OF VIEW DURING VIDEO GUIDED CLINICAL PROCEDURES USING REAL-TIME IMAGE PROCESSING

CROSS-REFERENCE TO RELATED APPLICATIONS

This application is a 35 U.S.C. § 371 national phase of PCT International Application No. PCT/US2020/054640, filed Oct. 7, 2020, which claims priority to and the benefit of U.S. Provisional Patent Application No. 62/911,986, filed Oct. 7, 2019 ("'986 application") and U.S. Patent Application No. 62/911,950, filed on Oct. 7, 2019 ("'950 application"). All the noted applications are hereby incorporated herein by reference in their entireties for all purposes.

FIELD

The disclosure generally relates to the fields of computer vision and image processing, and in particular, but not by way of limitation, the presented disclosed embodiments can be used for enhanced visualization in video guided minimally invasive clinical procedures of surgery and diagnosis, such as arthroscopy, laparoscopy or endoscopy, for the purposes of changing the direction of view of the surgical camera with an endoscopic lens, in which case the system renders the view that would be acquired by a physical scope with a different lens cut from the one that is being effectively used, or performing zoom along an arbitrary viewing direction without decreasing the image field-of-view or losing image contents.

BACKGROUND

In video-guided procedures, such as arthroscopy or laparoscopy, the anatomical cavity of interest is accessed through small incisions designated as surgical ports. One of these ports gives access to a video camera equipped with a rigid endoscope that enables the surgeon to visualize the interior of the cavity for the purpose of guidance during procedures of surgery or diagnosis. The rigid endoscope is an elongated tubular structure that is inserted into the body cavity. The endoscope typically comprises an objective lens at the distal end, an image-forwarding system, such as a series of spaced-apart lenses, and an ocular lens at the proximal end where a camera means, such as a charge coupled device (CCD) chip, is usually mounted. The image-forwarding system serves to forward the image from distal to proximal end. The camera receives this image and produces a signal for a video display to be observed by the surgeon.

The rigid endoscope, also referred to in here as lens scope or endoscopic lens, is used in different specialties and, depending on its features and application field, it can be alternatively named as arthroscope (orthopeadics), laparoscope (abdominal surgery), cystoscope (bladder), sinuscope (ENT), neuroscope, etc. The endoscopic camera, that results from combining a rigid endoscope with a camera means, has specific features that are uncommon in conventional cameras. The optics are usually exchangeable for the purpose of easy sterilization, with the endoscope being assembled in the camera head by the surgeon before starting the procedure. The ocular lens (or eye-piece) in the proximal end of the endoscope is assembled to the camera using a connector that typically allows the user to rotate the scope with respect to the camera head by an angle $\alpha$. This is a rotation in azimuth around a longitudinal axis of the endoscope, henceforth referred to as mechanical axis, that is close, but not necessarily coincident, with the symmetry axis of the tubular structure.

The rigid endoscope typically has a Field Stop Mask (FSM) somewhere along the image forwarding system that causes the acquired image to have meaningful content in a circular region which is surrounded by a black frame (which black frame is illustrated in diagonal lines in the figures of this application). The design of the FSM is such that there is usually a mark in the circular boundary defined by the image-frame transition that enables the surgeon to infer the angle in azimuth $\alpha$. This mark in the periphery of the circular image will be henceforth referred to as the notch.

In addition, the lens in the distal end of the endoscope is often mounted in such a way that the optical axis of the entire lens system has an angular offset from the longitudinal or mechanical axis of the scope. This angle $\beta$ between optical and mechanical axes is usually referred to as the lens cut of the endoscope. If the lens cut is different from zero, then the optical and mechanical axes are not aligned and the surgeon can vary the direction of view in azimuth by rotating the scope around the mechanical axis without having to move the camera head.

A variable Direction of View (DoV) enables the surgeon to change the endoscopic viewing direction without having to change the position of the endoscope itself. This is useful to see structures which are beside or behind the tip of the endoscope whenever the endoscope shaft cannot be easily moved because of anatomical constraints or constraints imposed by other surgical instruments in the operative field. Thus, variable DoV is definitely a desirable feature that affords the surgeon greater flexibility in his/her procedural approach. As discussed, the rigid endoscopes currently used in clinic empower the surgeon with the possibility of varying the DoV by performing a rotation in azimuth of the lens scope, which causes the optical axis to describe a cone in space with apex close to the projection center O (the cone of DoV). The half-angle of this cone is defined by the lens cut $\beta$ that is fixed and known a priori by the surgeon. Surgeons rely heavily on the prior knowledge of the lens cut of a particular endoscope to dependably know what the anatomy should look like.

There are endoscopes with different angular offsets from the longitudinal or mechanical axis, with the most commonly used lens cuts being 0°, 30°, 45° and 70°. Surgical procedures typically require endoscopes of most of these cut angles with specific emphasis on one of them. For example, in knee arthroscopy the preference goes for a lens cut of 30° that provides both a good forward view and a certain amount of lateral viewing, while in hip arthroscopy the lens cut of choice is usually 70° because the anatomic cavity is much narrower. In a similar manner, the preference in laparoscopy can vary between a lens cut of 0° (forward looking scope) or 30°. However, and despite the emphasis in a particular lens cut angle, most procedures can benefit from different lateral and partial retro-viewing angles at different moments or steps of the surgery. Unfortunately, and since a lateral change in DoV requires to physically exchange the endoscope to one with a different lens cut, the surgeons rarely do it in practice even when they realize that such change can improve visualization to accomplish the task at hands. Changing the endoscope in the middle of the procedure is cumbersome (both light and camera cables have to be disconnected and reconnected), time consuming, and sometimes dangerous. For example, the insertion of off-angle endoscopes can be dangerous because they are not looking in the direction they are being inserted, and neurosurgeons often refrain from using endoscopes with 45° or 70° lens cuts because they are afraid of blindly thrusting the endoscope into delicate tissue.

In summary, the rigid endoscopes commonly used in medicine enable the surgeon to vary the DoV in azimuth (angle α) but not in inclination or elevation (angle β), in which case the optical axis is constrained to move in a cone with symmetry axis aligned with the mechanical axis and angle defined by the lens cut β (the cone of DoV). It follows from the discussion that unconstrained variation of DoV would be highly beneficial namely by allowing the surgeon to change the lateral viewing angle (the lens cut β) without having to physically change the endoscope in the mid procedure. Several specially designed endoscopes, that allow angular shift of the direction of view both in azimuth and in inclination, have been disclosed (US2016/02.09A1, US20050177026A1, US2012/0078049, U.S. Pat. No. 9,307, 892). Unfortunately, these endoscopes use a movable image sensor or optical element at the distal end to change the lens cut β. Because of these moving parts, fabricating these scopes is complicated and costly, and such scopes are less robust than traditional fixed lens cut scopes. Also, they often deliver inferior illumination and image quality.

An alternative manner for accomplishing unconstrained variation of DoV is to employ computational means to process the endoscopic image or video. It is well known in the field of computer vision that a change in the DoV corresponds to a rotation of the camera around an axis going through its projection center, and that the virtual image that would be acquired by such rotated camera can be rendered by warping the real source image by a suitable homographic map often referred to as a collineation of the plane at infinity. The method is used in patent application US005313306A, US 20154/0065799A1, and EP3130276A1 that disclosed rigid endoscopes with wide angle lenses for hemispherical Field-of-View (FoV), that are combined with computer means to render images with a variable DoV that cover selected parts of the FoV. The result are camera systems with controllable pan-and-tilt orientation where the user commands the viewing direction both in X (azimuth) and Y (elevation) using electronic means.

A problem of these systems is that in the context of endoscopy and video-guided clinical procedures the surgeon is used to changing the viewing direction in azimuth by simply rotating the lens scope with respect to the camerahead. Thus, moving the control from mechanical to electronic can be challenging, require surgical re-training, and become a major obstacle for broad adoption.

What is desired, therefore, is an endoscopy system with a DoV that can vary both in azimuth α and inclination β, where the variation in azimuth is accomplished by the standard mechanical means, i.e. by rotating the rigid endoscope with respect to the camera head, and the variation in inclination is accomplished by electronic or computer means, i.e. by using real-time processing to render images with the targeted viewing direction.

It is still further desired to provide an endoscopy system that operates in the standard manner but where the user has the possibility to electronically switch between rigid endoscopes with different lens cuts for optimum visualization conditions at all times.

Additionally, it is desired to provide an endoscopy system where the user can control the amount of image radial distortion to either work with distortion free images for optimal perception of scene depth, or to select a Region of Interest by varying the DoV and magnify it while preserving the FoV and maintaining all visible contents in image.

SUMMARY

Systems and methods that use real-time image processing to change the direction of view during video-guided clinical procedures of surgery and diagnosis, while allowing the surgeon to physically rotate the lens scope with respect to the camera-head as is current common practice in different surgical procedures such as arthroscopy, laparoscopy and endoscopy.

The presently disclosed embodiments disclose a software-based system that enables to change the viewing direction of a particular scope by an arbitrary amount γ such that the cutting angle of the lens (or lens cut) virtually switches from β to α+γ. This is accomplished in a seamless, fully automatic manner that is realistic for the user that can physically rotate the endoscope in azimuth around its longitudinal axis during operation.

A software-based system processes the images and video acquired by an endoscopy camera equipped with a lens with a wide Field of View (FoV) to empower the surgeon with electronic switch between two or more virtual endoscopes with different lens cuts.

In addition, the presently disclosed embodiments disclose a method that, given the desired lens cuts $\hat{\beta}_1$ and $\hat{\beta}_2$ and FoVs $\hat{\Theta}_1$ and $\hat{\Theta}_2$ of the two targeted virtual endoscopes, determines the lens cut β and FoV Θ of the source camera such that the acquired images and video are well suited to be used as input in the disclosed image processing methods for rendering realistic virtual images and video.

The presently disclosed embodiments disclose a method that, given arbitrary pre-sets for the virtual camera, not only in terms of desired shift in lens cut γ, but also in terms of image resolution m×n, field-of-view $\hat{\Theta}$, and amount of image distortion $\hat{\xi}$, assures that the corresponding virtual view is correctly rendered without top or bottom regions without content (empty regions) by automatically adjusting the focal length f̂ and position of principal point Ô at each frame time instant.

The presently disclosed embodiments disclose a method that enables to control the amount of image radial distortion to either work with distortion free images for optimal perception of scene depth, or to select a Region of Interest by performing image zoom along arbitrary viewing directions by either changing the amount of radial distortion $\hat{\xi}$, in which case the zoom is accomplished without loss in the field of view (FoV), or by changing the focal length f.

BRIEF DESCRIPTION OF THE DRAWING

For a more complete understanding of the present disclosure, reference is made to the following detailed description of exemplary embodiments considered in conjunction with the accompanying drawings.

FIG. 10 (a) shows a part of the interior of the target boundary being mapped beyond the boundary of the source image, leading to an empty region in the bottom without image content. FIG. 10 (b) shows a trivial solution that is to estimate the focal length $\hat{f}$ such that the point that is farthest from the source boundary moves to be coincident with it. Unfortunately, this approach decreases the FoV, which is undesirable. FIG. 10 (c) shows the proposed solution where both the focal length $\hat{f}$ and the principal point $\hat{O}_i$ are simultaneously adjusted to remove the empty regions, while avoiding a reduction in the desired FoV.

DETAILED DESCRIPTION

It should be understood that, although an illustrative implementation of one or more embodiments is provided below, the various specific embodiments may be implemented using any number of techniques known by persons of ordinary skill in the art. The disclosure should in no way be limited to the illustrative embodiments, drawings, and/or techniques illustrated below, including the exemplary designs and implementations illustrated and described herein. Furthermore, the disclosure may be modified within the scope of the appended claims along with their full scope of equivalents.

Systems and methods for changing the direction of view during video guided clinical procedures are disclosed herein. The systems and methods may be used for clinical procedures including, but not limited to, arthroscopy, laparoscopy, endoscopy or other surgical procedures including minimally invasive orthopedic surgery procedures. The systems and methods can be used with real-time image processing or delayed image processing.

Figure 1:
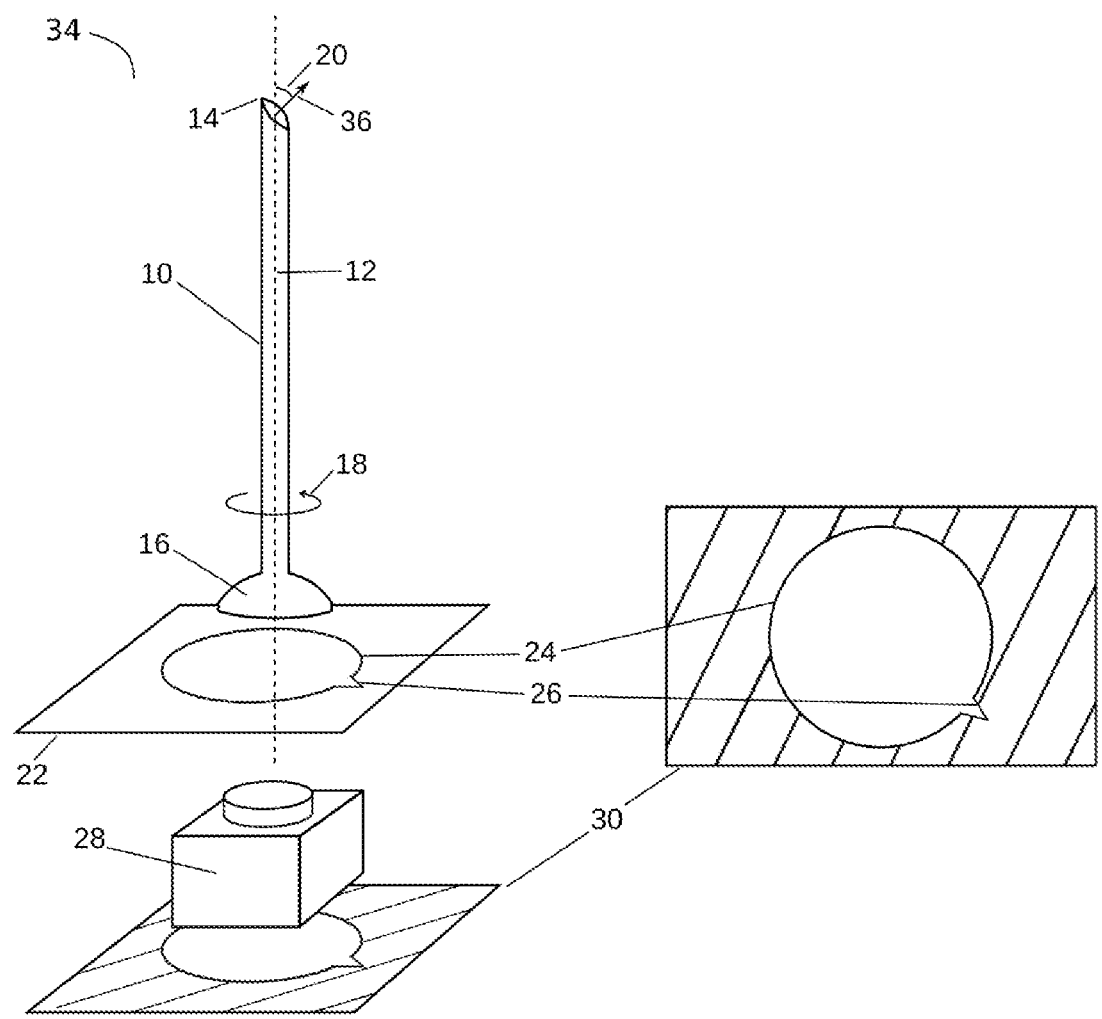
FIG. 1 is an embodiment of an endoscopic camera comprising an endoscope and a camera head, and showing all its constituent parts. The canonical image that is formed by the endoscope that contains a Field Stop Mask (FSM) in its image forwarding system is depicted, as well as the image in pixels obtained after the application of the intrinsic parameters by the sensor in the camera head.

FIG. 1 schematizes an endoscopic camera 34, to be used in the aforementioned video guided clinical procedures, that consists of an endoscope 10 whose proximal end 16 is assembled to a camera head 28 by means of a connector that allows the endoscope 10 to perform a rotation in azimuth by an angle α 18 around the mechanical axis 12. The endoscope 10 typically contains a Field Stop Mask (FSM) along the image forwarding system that causes the light that is forwarded from the distal end 14 to the proximal end 16 to form a canonical image 22 containing a circular boundary 24 and a notch 26. The camera head 28 transforms the canonical image 22 into an image in pixels 30 also presenting a circular boundary 24 and a notch 26. Moreover, and as discussed in the background section, the direction of view (DoV) 36 changes while rotating the endoscope 10 with respect to the camera head 28 because of the lens at the distal end 14 that causes the optical axis 36 and the mechanical axis 12 to be misaligned by an angle β denoted as lens cut 20.

Figure 2:
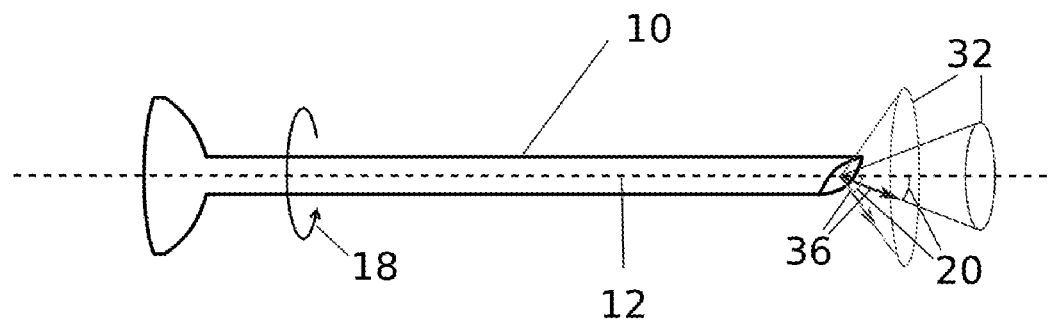
FIG. 2 is an embodiment of an endoscope, showing two different directions of viewing (DoV) that give rise to two distinct cones of DoV. Each cone corresponds to the trajectory described by the optical axis while the endoscope rotates around the mechanical axis.

The rotation in azimuth 18 around the mechanical axis 12 of the endoscope 10 causes the optical axis 36 to describe a cone in space 32 (the cone of DoV) whose half-angle is the lens cut 20, as illustrated in FIG. 2.

In this disclosure, 2D and 3D vectors are written in bold lower and upper case letters, respectively. Functions are represented by lower case italic letters, and angles by lower case Greek letters. Points and other geometric entities in the plane are represented in homogeneous coordinates, as is commonly done in projective geometry, with 2D linear transformations in the plane being represented by 3×3 matrices and equality being up to scale. In addition, when representing functions, the symbol ; is used to distinguish between variables (that appear to the left of ;) and parameters (that appear to the right of ;) of the function. Finally, different sections of the text are referenced by their paragraphs' numbers using the symbol §.

Image Warping

The disclosed methods and systems for the rendering of virtual views with an arbitrary shift in the inclination of viewing direction relate with image warping techniques, in particular with software based methods to create a virtual Pan-Tilt-Zoom (PTZ) camera from a wide Field of View (FoV), panoramic camera. In this case, the image that would be acquired by the PTZ camera (the target image) is rendered from the image acquired by the panoramic camera (the source image) through a function that maps pixels in one image into pixels in the other.

Figure 3:
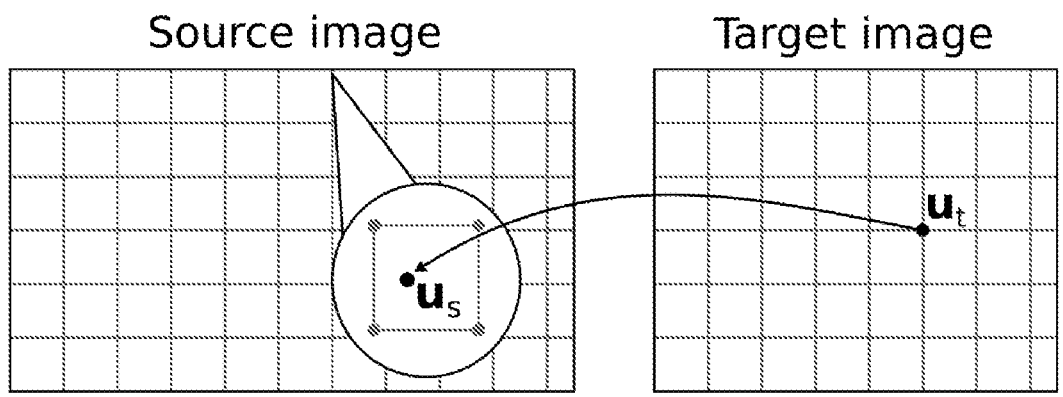
FIG. 3 illustrates the image warping process between a source and a target image, with the color of the pixels in the target image being obtained using an interpolation scheme. The warping function is the composition of the source and target camera models $c_s$ and $c_t$ with a motion model m.

Without loss of generality, let w be the function that transforms pixel coordinates $u_t$ in the target image into pixel coordinates $u_s$ in the source image, as illustrated in FIG. 3. The color value of pixel $u_t$ in the target image can be determined by using any type of interpolation approach in the spatial or in the frequency domains, which includes, but is not limited to, nearest neighbors, next neighbors, previous neighbors, bi-linear, bi-cubic, Lanczos, bi-cubic b-spline, Mitchell-Netravali, Catmull-Rom, Kriging based, wavelet based, or edge-directed interpolation. Data driven interpolation filters learned using machine learning or deep learning can also be employed for obtaining the color value of $u_t$.

The existing warping techniques include, but are not limited to, direct mapping, inverse mapping, warping by re-sampling in the continuous or discrete image domain, warping by re-sampling and filtering, warping using a look-up table, warping using decomposable transformations and learned warping transformations.

The warping function w is the composition of functions $c_s$ and $c_t$, corresponding to the camera models of the source and target cameras, respectively, with function m, which is the camera motion. The camera models $c_s$ and $c_t$ describe the mapping between the canonical image 22 in millimeters and the image in pixels 30. Since the source camera is a real camera, $c_s$ can be determined using an appropriate calibration method. On the other hand, the target camera $c_t$ is chosen so that the desired imaging features (resolution, zoom, FoV, etc) are predefined. Concerning function m, it describes the relative motion between virtual (target) and real (source) cameras. In more detail, it represents the rotation undergone by the virtual camera in 3D space that causes an homography mapping in projective coordinates between the canonical images of the source and target cameras.

Warping images acquired with endoscopic cameras is significantly more challenging than doing so with images acquired with conventional cameras because of two main reasons. Firstly, the camera model $c_s$ changes in every frame time instant due to the relative rotation of the endoscopic lens with respect to the camera head, and this must be taken into account in building the warping function w. Secondly, the motion model m depends not only on the desired change in elevation γ but also in the mechanical change in azimuth δ that must be measured at every frame time instant. These challenges do not exist for conventional cameras because they do not present moving parts that interfere with the camera model.

Endoscopic Camera Model

This section introduces the endoscopic camera model c by describing the model of a general camera presenting radial distortion introduced by the optics, providing an overview of relevant concepts and explaining how the endoscopic camera can be described with an adaptive model that is updated at every frame time instant.

General Camera Model

Figure 4:
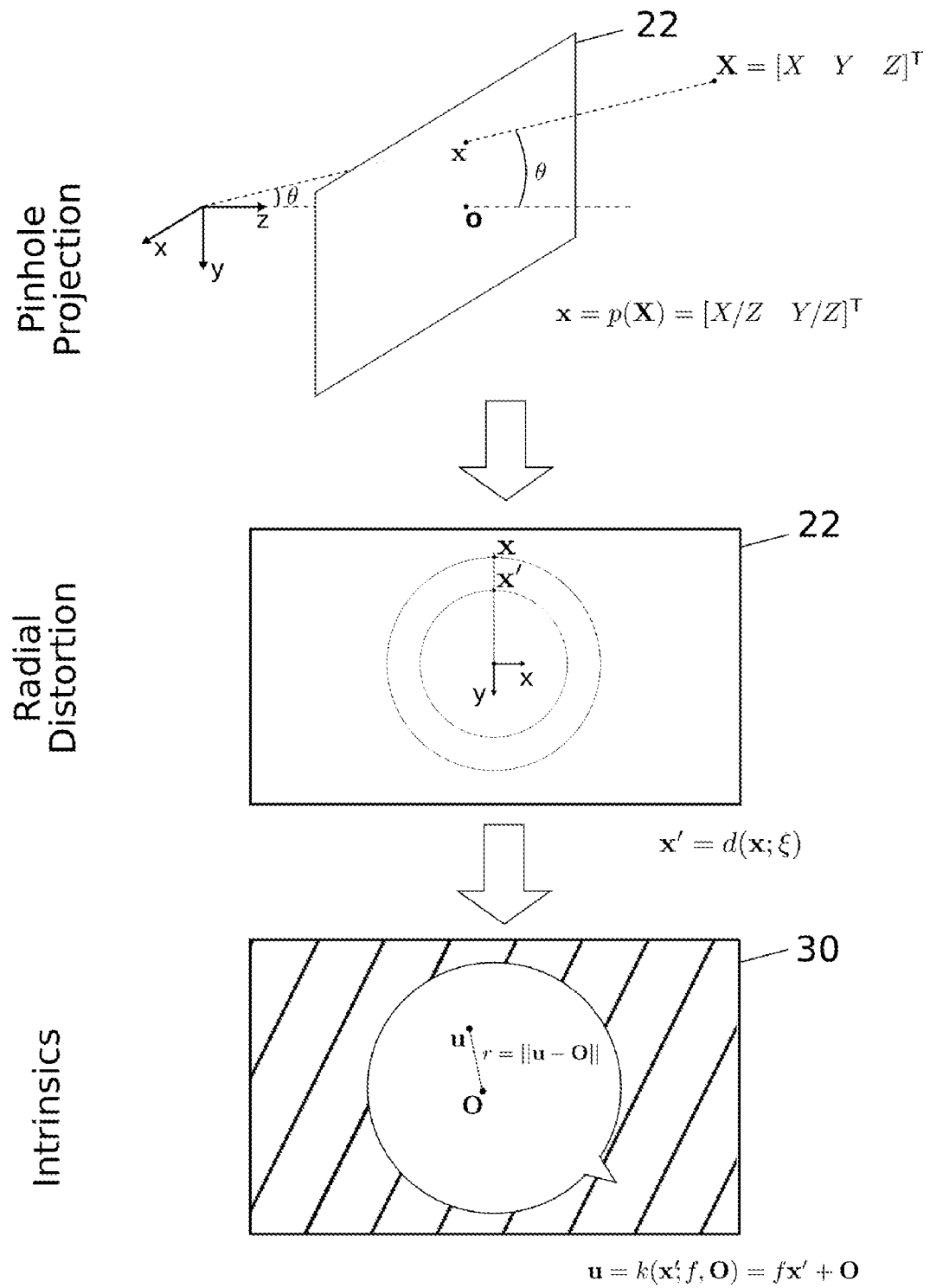
FIG. 4 schematizes the process of obtaining camera model c. A 3D point X is projected onto the image plane according to the pinhole model, yielding a 2D point x in the canonical image. Afterwards, distortion d is an operation performed in the canonical image that applies distortion to point x, yielding point x'. As a final step, the application of the intrinsic parameters by function k converts points in millimeters x' into points u in the image in pixels. The camera model c is a function applied in 2D space that transforms points x in the canonical image into points u in the image in pixels, $u=c(x; f, O, \xi)$ and is obtained by the composition of the distortion d and the intrinsics k: $c=k \cdot d$.

FIG. 4 schematizes the different steps that comprise the camera model function c. A 3D point $X=[X\ Y\ Z]^T$ is projected onto the image plane according to the pinhole model, yielding a 2D point x in the canonical image 22. This projection is denoted asp and corresponds to computing $x=p(X)=[X/Z, Y/Z]^T$. Afterwards, distortion d is an operation performed in the canonical image 22 that applies distortion to point x, yielding point x': $x'=d(x;\xi)$, with ξ being the distortion parameters. As a final step, the application of the intrinsic parameters converts points in millimeters x' into points u in the image in pixels 30. This is accomplished through function k by computing u=k(x'; f, O)=fx'+O, with f being the focal distance, O the principal point and assuming, without loss of generality, that the pixels are squared, i.e., the aspect ratio is unitary and the skew is zero. In case this assumption is not made, it is straightforward to update function k to include two extra parameters that account for the aspect ratio and the skew. The camera model c is a function applied in 2D space that transforms points x in the canonical image 22 into points u in the image in pixels 30, u=c(x; f, O, ξ) and is obtained by the composition of the distortion d and the intrinsics k: c=k·d.

In this model, the distortion function d is generic, meaning that it can be any distortion model in the literature such as Brown's polynomial model, the rational model, the fish-eye model, or the division model with one or more parameters, in which case ξ is a scalar or a vector, respectively. The distortion function d can also take into account other types of distortion such as, but not limited to, tangential distortion, prism distortion or perspective distortion caused by tilt of the sensor. Without loss of generality, it is assumed in the remainder of the description that d applies the first order division model, with ξ being a scalar:

$$x' = d(x; \xi) = \begin{bmatrix} x \\ y \end{bmatrix} \frac{1}{1 + \xi\sqrt{x^2 + y^2}}.$$

Moreover, it is known that a distance r in pixels measured in the image in pixels 30 between a point u and the principal point O (r=‖u−O‖) corresponds to an angle θ in 3D that depends on the joint effect of f and ξ, such that $$\Phi(f, \xi, \theta, r) = 0. \quad (1)$$

Handling Lens Rotation

Figure 5:
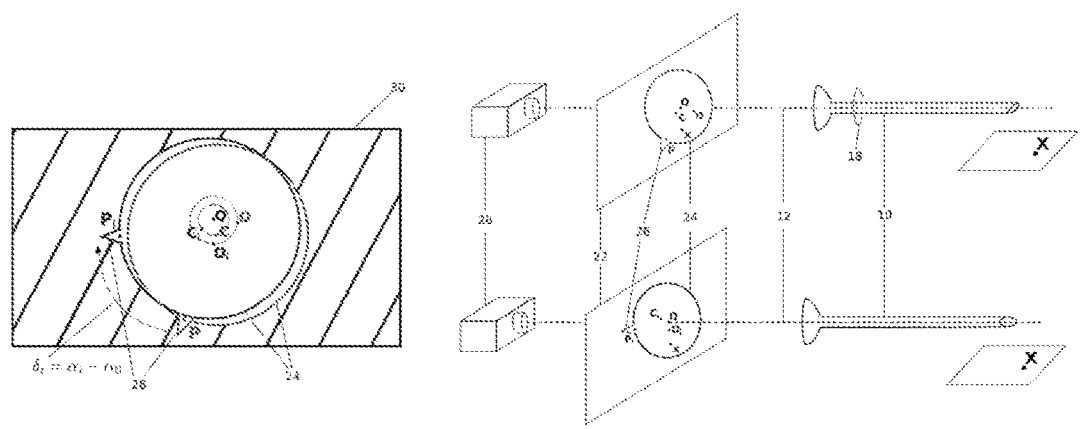
FIG. 5 illustrates the effect of the scope rotation in the location of the boundary and the principal point O. The scope rotates around the mechanical axis that intersects the image plane in the rotation center Q. The FSM is projected onto the image plane as a circle with center C, and the mark in the FSM is projected onto a point P, referred to as notch. When the scope rotates by an angle $\delta_i$, the circle center C, notch P and principal point O also rotate by that same amount $\delta i$, around Q.

The rotation of the endoscope 10 with respect to the camera head 28 causes the principal point O, the center C of the circular boundary 24 and the notch 26, denoted as P, to rotate in the image in pixels 30 around a point Q, as illustrated in FIG. 5. In fact, O and C rotate around Q because they are usually not coincident due to mechanical tolerances during lens manufacturing. Knowing that O is the image of the optical axis, C is the center of the circular boundary that depends on how the FSM is placed with respect to the lens rod and Q is the intersection of the mechanical axis 12 with the image plane, which depends on the eye-piece, the coincidence of all three points occurs when the eye-piece and the FSM are perfectly aligned with the lens rod. The misalignment between Q and C causes the boundary to change positions in the image and C to move in a circle around Q while the lens rotates. When Q and O are misaligned, O also describes a circular trajectory around Q.

Thus, if the calibration parameters f, O, ξ refer to a particular azimuth position $\alpha_0$, then a rotation in azimuth by an angle $\delta_i = \alpha_i - \alpha_0$ changes the position of the principal point to $O_i = r(O; \delta_i, Q)$, where r denotes a 2D rotation by an angle $\delta_i$ around an axis going through Q. Similarly, the center of the circular boundary becomes $C_i = r(C; \delta_i, Q)$.

In other words, let f, O and ξ be the calibration parameters of a generic endoscopic camera at a particular azimuth position $\alpha_0$. It comes that the camera model that maps points x in the canonical image into points u in pixel coordinates can change at every frame time instant i, being given by u=c(x; f, $O_i$, ξ) with $O_i = r(O; \delta_i, Q)$ and $\delta_i = \alpha_i - \alpha_0$, where $\alpha_i$ is the angle in azimuth in frame i.

In the remainder of this description, it is assumed, without loss of generality, that both the calibration parameters f, O, ξ for a reference azimuth position $\alpha_0$ and the rotation center Q are known a priori, such that if rotation $\xi_i$ with respect to $\alpha_0$ is estimated at each frame time instant i, then the calibration parameters f, $O_i$, ξ can be determined as previously described. It is relevant to note that if O is coincident with Q, then $O_i$ in every frame i will also be coincident with Q and thus this adaptation of the camera model c to the rotation of the scope is unnecessary. However, the misalignment between these entities occurs frequently due to mechanical tolerances in building the optics, as discussed previously. Since the effect of this misalignment in the calibration parameters is not negligible, it must be taken into account in practice.

Camera Rotation Motion in 3D

Figure 6:
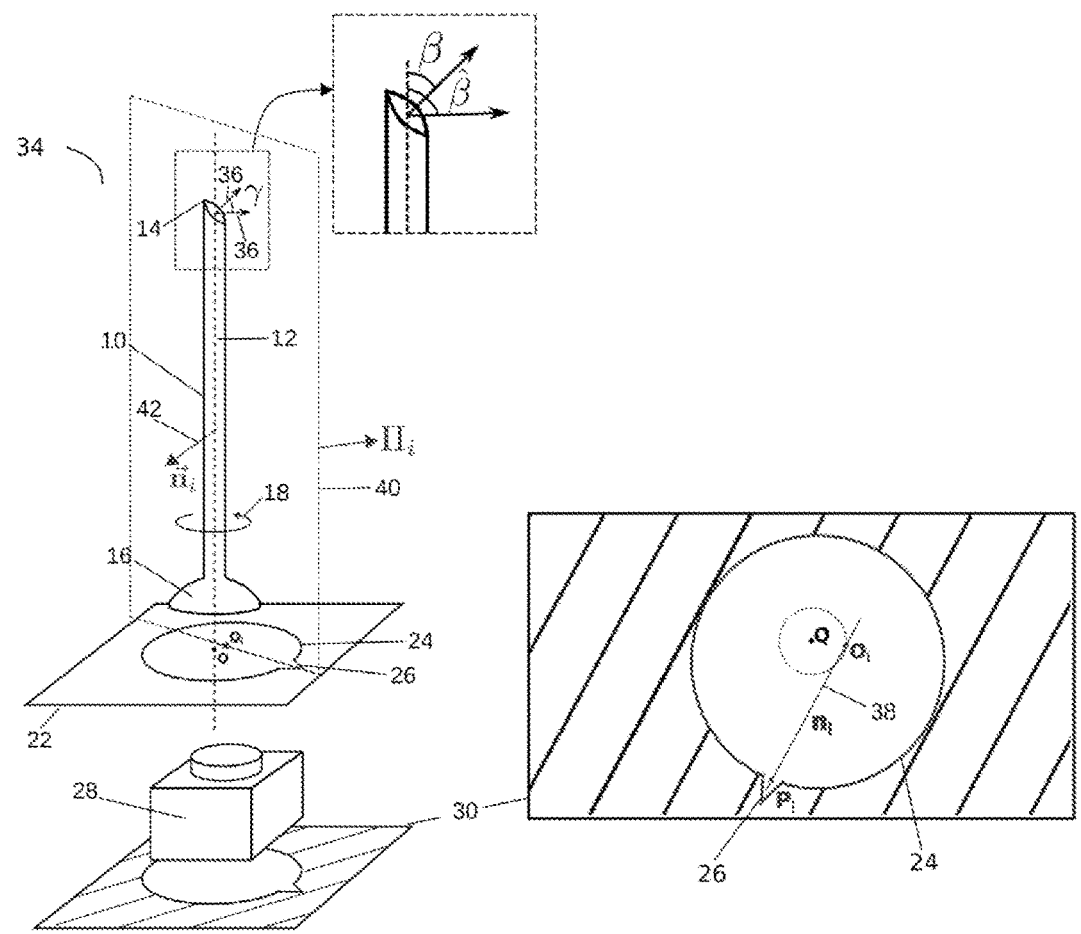
FIG. 6 illustrates the relevant entities in the estimation of the motion model m, which is a 3D rotation by an angle $\gamma=\hat{\beta}-\beta$ around axis $\vec{n}_i$. This rotation is the virtual motion the real camera with lens cut $\beta$ must perform in order to virtualize a camera with lens cut $\hat{\beta}$. Direction $\vec{n}_i$, which is the normal to the reference plane $\Pi_i$, is estimated by detecting line $n_i$ in every frame i and back projecting it into the 3D space.

The method to determine the motion model m introduced in the section titled Imaging Warping is now described, with the accompanying FIG. 6 providing an illustrative scheme to better explain the most relevant concepts. As previously mentioned, a change in the DoV of a generic camera can be accomplished by rotating the camera around an axis going through its projection center. In our particular case of endoscopic cameras, the virtualization of a camera with lens cut $\hat{\beta}$ from a real camera with lens cut β corresponds to a change in the DoV that can be accomplished by virtually rotating the real camera in 3D about its center of projection by an angle $\gamma = \hat{\beta} - \beta$ around a direction $\vec{n}_i$ 42. This direction $\vec{n}_i$ 42 is the normal to a plane $\Pi_i$ 40, henceforth referred to as the reference plane, that is defined by the mechanical and optical axes, which, in ideal conditions, are coplanar but not coincident because of the non-zero lens cut. Since the optical axis 36 defines the DoV that changes with the rotation in azimuth 18, the motion model m, which is a 3D rotation of γ around axis $\vec{n}_i$ 42, can vary at every frame time instant i and must be estimated accordingly.

As illustrated in FIG. 6, the reference plane $\Pi_i$ 40 is projected into a line $n_i$ 38 in the image in pixels 30. Thus, it is possible to determine $\vec{n}_i$ on-the-fly by detecting line $n_i$ 38 in every frame i and back-projecting it into the 3D space.

In ideal conditions, plane $\Pi_i$ 40 contains both the optical and the mechanical axes and intersects the FSM in the notch, whose purpose is to inform the surgeon about the direction of the lens cut. These conditions hold if and only if points Q, $O_i$ and $P_i$ in the image in pixels 30 are collinear and, in this case, line $n_1$ 38 is the line that contains all three points Q, $O_i$, and $P_i$. In real conditions, this does not usually happen due to the mechanical tolerances in lens manufacturing, leading to a non-coplanarity of the optical and mechanical axes and/or plane $\Pi_i$ 40 not going exactly through the notch of the FSM. Thus, in the remainder of this description, it is assumed, without loss of generality, that $n_i$ 38 is the line defined by the optical axis $O_i$ and the notch $P_i$. Thus, in projective coordinates, line $n_1$ 38 is computed by $n_i = P_i \times O_i$ and the normal to plane $\Pi_i$ 40 can afterwards be determined in a straightforward manner by $\vec{n}_i = K_i^T n_i$ with $K_i$ being the matrix of intrinsic parameters in frame i, $$K_i = \begin{bmatrix} f & 0 & O_{ui} \\ 0 & f & 0_{vi} \\ 0 & 0 & 1 \end{bmatrix} \text{ and } O_i = [O_{ui}, O_{vi}]^T.$$

Alternatively, since in ideal conditions points Q, $O_i$ and $P_i$ in the image in pixels 30 are collinear, as is the boundary center $C_i$, line $n_i$ 38 can be obtained by determining the line that goes through points Q and $O_i$ or $C_i$ and $O_i$, in which case points Q and $C_i$ replace $P_i$ in the previous equation, respectively.

Further Considerations

In this disclosure, it is assumed, without loss of generality, that all measurements and computations are performed in dry environment. Adaptation to wet environment can be performed in a straightforward manner by multiplying the focal length by the ratio of the refractive indices of the two or more mediums where light travels before reaching the imaging sensor.

Figure 7:
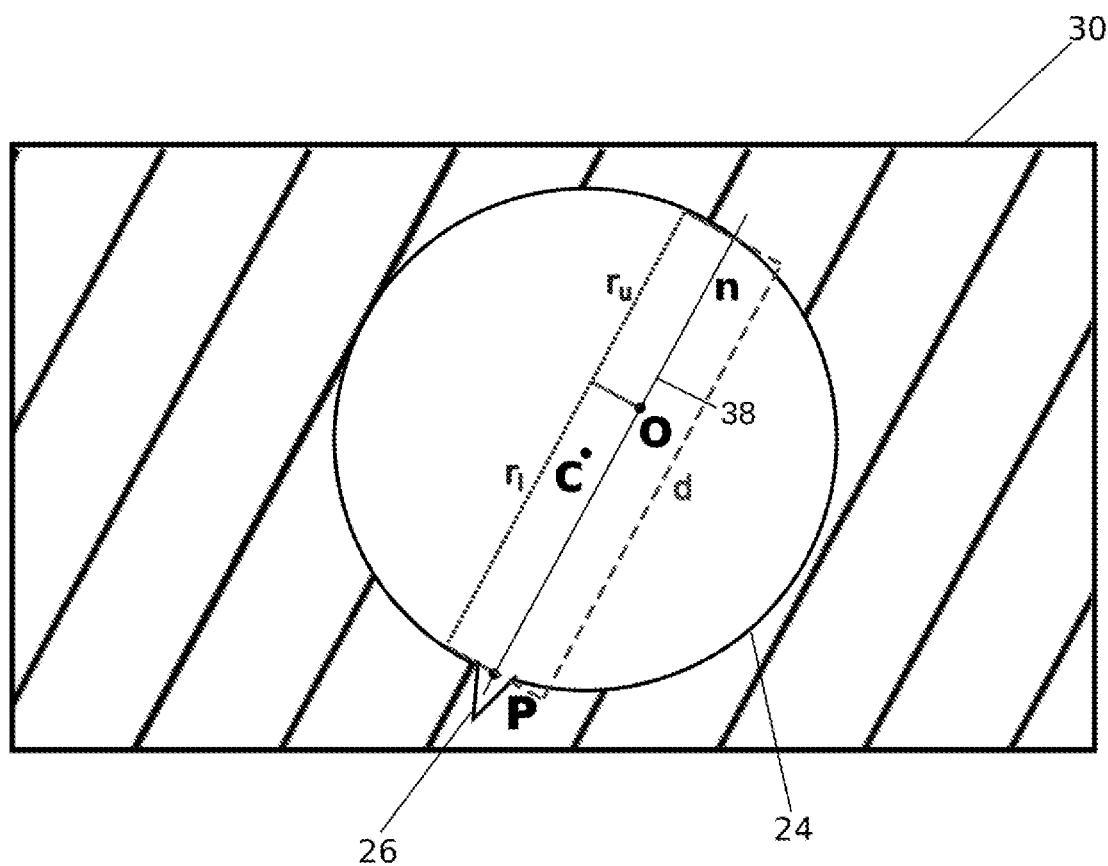
FIG. 7 illustrates the concept of diameter d, which is the length of the segment whose endpoints are the intersections of a line that contains the principal point O with the boundary. Diameter d is used to determine the Field of View (FoV) $\Theta$ of the camera. The figure shows the particular case of the line going through the notch P.

Another important consideration to make is that both the update of the camera model c and the detection of line $n_i$ 38 in the image in pixels 30 in every frame i can be performed by determining the angular displacement in azimuth $\delta_i$ with respect to a reference angular position $\alpha_0$, which may be accomplished using exclusively image processing techniques. In this disclosure is it considered, without loss of generality, that the method disclosed in U.S. Application No. 62/911,950 for detecting the boundary with center $C_i$ and notch $P_i$ in every frame i is employed for this task. This method contemplates the possibility that the FSM contains more than one notch, which is useful for guaranteeing that at least one notch is always visible in the image, being able to detect multiple notches whose relative location is known and that are identified by their different shapes and sizes. Thus, it comes that the angular displacement $\delta_i$ is the angle defined by points $P_i$, Q and P ($\delta_i = \sphericalangle PQP_i$), with P being the position of one of the notches at the reference angular position $\alpha_0$. Alternatively, $\delta_i$ can be estimated from the boundary centers $C_i$ and C, with C being the center of the boundary in the reference position: $\delta_i = \sphericalangle CQC_i$ As discussed with respect to Equation (1) above, a distance r measured in the image in pixels 30 between any point and the principal point O corresponds to an angle $\theta$ in 3D that depends on both f and $\xi$ and that can be computed using Equation 1. Let d be the length of the line segment whose endpoints are the two intersections of the boundary with the line n 38 in FIG. 7 that goes through the principal point O. This length d is referred to as diameter despite not corresponding to the diameter of the circular boundary, as this only happens in case the principal point O is coincident with the boundary center C. As illustrated in FIG. 7, d is the addition of a lower and an upper radius: $d=n+r_u$. Using both n and $r_u$, angles $\theta_l$ and $\theta_u$ can be determined from Equation 1. The field of view (FoV) of the camera $\Theta$ is defined as the addition of these two angles: $\Theta=\theta_l+\theta_u$. Any line n going through the principal point O defines a different diameter d, and FIG. 7 shows the particular case of n going through the notch P.

Method for Changing the Direction of View (DoV)

This section presents the method disclosed in this disclosure for changing the DoV by rendering the video that would be acquired by a virtual camera with predefined characteristics located in the same 3D position as a real endoscopic camera. In particular, let $I_i$ be frame i acquired by the real endoscopic camera, henceforth referred to as the source camera, whose endoscope has a lens cut $\beta$ and rotates in azimuth around a mechanical axis that intersects the image plane in the rotation center Q. The endoscopic camera's calibration for a reference angular position $\alpha_0$, corresponding to a particular notch position P, is known, meaning that its focal length f, radial distortion $\xi$ and principal point O have been determined. The purpose of this method is to render an image $\hat{I}_i$ with resolution m×n and a circular boundary with diameter $\hat{d}$ centered in point $\hat{C}$ that would be acquired by a virtual camera, henceforth referred to as the target camera, with a lens cut $\hat{\beta}$, Field-of-View $\hat{\Theta}$, and distortion $\hat{\xi}$ placed in the same 3D location as the source camera.

Figure 8:
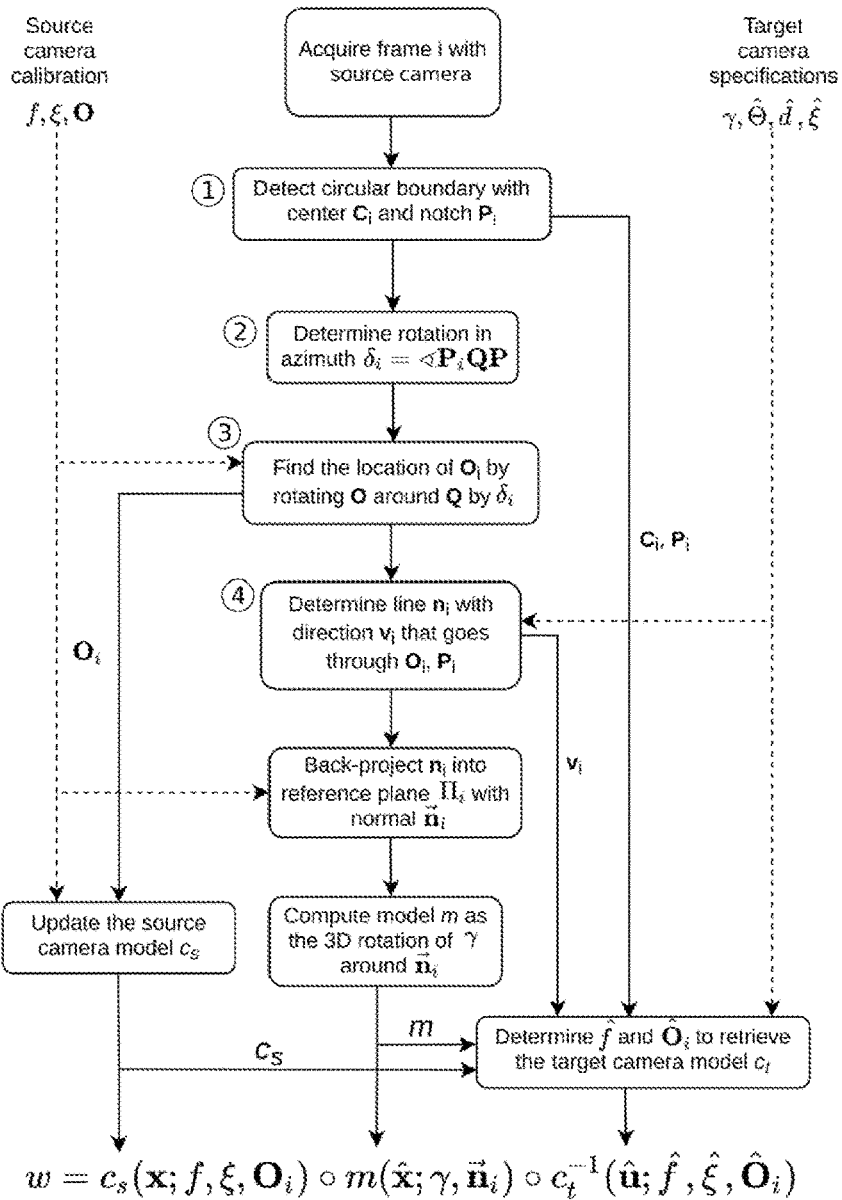
FIG. 8 schematizes the method disclosed in this disclosure for changing the direction of view by illustrating the steps that allow the rendering of the video that would be acquired by a virtual camera with predefined characteristics located in the same 3D position as a real endoscopic camera. The output of this method is a mapping function w that converts pixels û in the target image acquired by the virtual camera into pixels u in the source image acquired by the real camera.
Figure 8:
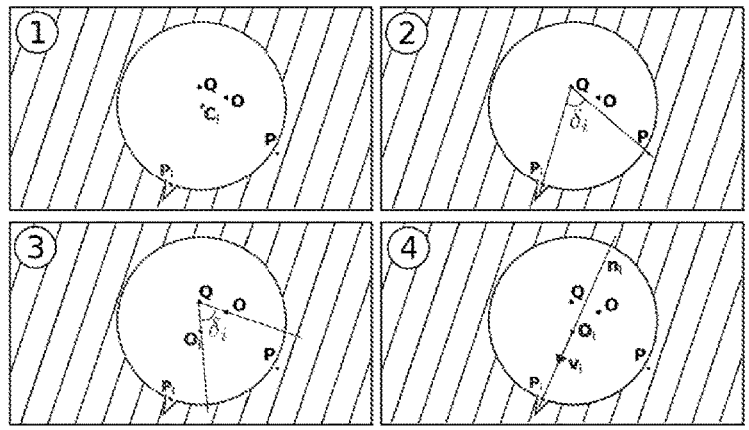

As shown in FIG. 8, the method starts by detecting the boundary with center $C_i$ and notch $P_i$ in image $I_i$. By determining the rotation in azimuth $\delta_i$ as the angle defined by points $P_i$, Q and P, it is possible to estimate the location of the principal point $O_i$ by rotating O by an angle $\delta_i$ around Q, as described in the section titled Handling Lens Rotation. This provides the updated model for the source camera $c_s$ that maps points x in the canonical image, which are the pinhole projection of points X in the 3D scene, into points u in the image in pixels, such that $u=c_s(x; f, O_i, \xi)$.

Line $n_i$, which is the projection of the reference plane $\Pi_i$ introduced in the section titled Camera Rotation Motion in 3D in the image plane, is determined as the line that goes through points $O_i$ and $P_i$. As previously described, by back-projecting $n_i$ into the 3D space, plane $\Pi_i$ with normal $\vec{n}_i$ can be obtained, yielding motion model m, which is a rotation in 3D space around axis $\vec{n}_i$ by an angle $\gamma$ that corresponds to the difference between the lens cuts of the target and source cameras, $\gamma=\hat{\beta}-\beta$. Motion model m transforms points $\hat{x}$ into points x in the canonical images of the target and source cameras, respectively, such that $x=m(\hat{x}; \gamma, \vec{n}_i)$.

In order to derive the camera model for the target camera $c_t$ that maps points $\hat{x}$ in its canonical image into points $\hat{u}$ in the image in pixels ($\hat{u}=c_t(\hat{x}; \hat{f}, \hat{O}_i, \hat{\xi})$), the focal length $\hat{f}$ and the location of the principal point $\hat{O}_i$ in every frame i must be computed. Details on the estimation of these parameters are given in the section below titled Adjusting the Target Camera Model.

As a final step, the algorithm generates the target image $\hat{I}_i$ using image warping techniques, as described in the section titled Image Warping, where each pixel $\hat{u}$ in $\hat{I}_i$ is mapped into a point u in the source image $I_i$ by the mapping function w, that is the composition of functions $c_s$, m and $c_t^{-1}$ ($w=c_s \cdot m \cdot c_t^{-1}$), such that the color value of $\hat{u}$ can be interpolated. As previously described, this mapping function w may implement any method for image warping or pixel value interpolation.

The disclosed method for changing the DoV assumes that the calibration parameters of the source camera for the reference position in azimuth $\alpha_0$ are known in advance. These can be determined in several different ways, which include, but are not limited to, using a set of calibration parameters predetermined in factory or representative of a set of similar endoscopic cameras and using an appropriate calibration method for performing calibration in the Operating Room before the medical procedure, such as the one disclosed in U.S. Pat. No. 9,438,897 (application Ser. No.

14/234,907) entitled "Method and apparatus for automatic camera calibration using one or more images of a checkerboard pattern".

In addition, the presently disclosed method also assumes that the rotation center Q is known a priori. However, this is not a strict requirement since Q may be determined on-the-fly from points $P_i$ and/or $C_i$ detected in successive frames, using the method disclosed in US Application No. U.S. Application No. 62/911,950. Another alternative is to determine the position of the principal point $O_i$ in every frame time instant i by making use of an estimate for the principal point given in a normalized reference frame that is attached to the circular boundary. In this case, since $O_i$ is obtained directly from the normalized estimate of the principal point, as disclosed in US Application No. U.S. Application No. 62/911,950, it is not required to know the rotation center Q or the angular displacement in azimuth $\delta_i$ a priori.

The estimation of the angular displacement in azimuth $\delta_i$, depicted in the second block of the diagram in FIG. 8, is performed using exclusively image processing methods. However, there are alternative estimation approaches that can be employed to measure the changes in rotation in azimuth of the scope with respect to the camera-head at every frame time instant. These include the use of sensing devices such as a rotary encoder attached to the camera head or an optical tracking system for determining the position of an optical marker attached to the scope cylinder.

The method for changing the DoV disclosed herein may be used for different purposes by setting the parameters of the target camera to desired values. In particular, if the distortion of the target camera $\hat{\xi}$ is set to zero, the images $\hat{I}_i$ rendered by the target camera will be distortion-free images. Also, in order to perfectly mimic a real endoscopic camera comprising an FSM, the rendered target images $\hat{I}_i$ may be processed to create a black frame such that meaningful image contents are within a circular region with center $\hat{C}$ and diameter $\hat{d}$ and to create a notch by placing a visual mark in point $\hat{P}_i=\hat{C}_i+\hat{d}/2\, v_i$ in the circular boundary, with $v_i$ being the unit direction of line $n_i$ ($v_i=P_i-O_i/\|P_i-O_i\|$) computed in block 4 of the diagram in FIG. 8. The image boundary can also take any other desired geometric shape, such as, but not limited to, a conic shape, a rectangular shape, a hexagonal shape or any other polygonal shape.

Adjusting the Target Camera Model

The disclosed warping function w is the composition of three functions: the camera model $c_s$, for which the parameters are the calibration parameters of the real source camera at the current frame i, the motion model m that depends on the desired change in inclination $\gamma$ and orientation $\vec{n}_i$ of the reference plane with respect to camera-head, and the camera model $c_t$ for the virtual target camera that must be such that the FoV is $\hat{\Theta}$ for an image distortion of $\hat{\xi}$ and image diameter $\hat{d}$.

While the two first functions are fully determined, it remains to define the focal length $\hat{f}$ and principal point $\hat{O}_i$ of the target camera to fully specify $c_t$.

Figure 9:
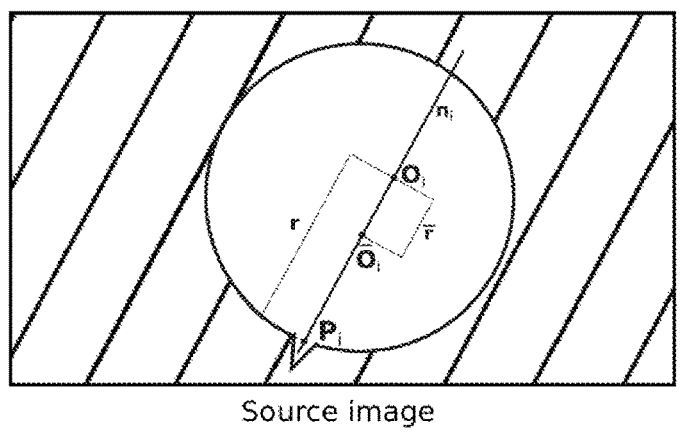
FIG. 9 illustrates how to compute point $\overline{O}_i$ in the source image, which is the point where the warping function will map the principal point of the target image $\hat{O}_i$. $\overline{O}_i$ can be determined by transforming the origin of the reference frame of the canonical image of the target camera $[0, 0]^T$ by a function g that is the composition of the camera model $c_s$ and the motion m ($g=c_s \cdot m$). Knowing point $\overline{O}_i$ allows to estimate the limiting viewing angle that is used in the methods of FIG. 10 to prevent the existence of empty regions in the target images.

Since both functions $c_s$ and m are known, it is possible to anticipate the location $\overline{O}_i$ where the principal point of the target image will be mapped by the warp function w in the source image (FIG. 9). Considering g to be the composition of $c_s$ and m, such that $g=c_s \cdot m$, it can be shown that the location is $\overline{O}_i=g(0)$ with 0 being the origin $[0, 0]^T$. This location is independent of the values of $\hat{f}$ and $\hat{O}_i$ that have not been selected yet.

The choice of parameters $\hat{f}$ and $\hat{O}_i$ for the target camera $c_t$ can be performed according to three different settings, for which an illustration is given in FIG. 10, as follows.

Setting A: One possibility is to choose $\hat{O}_i$ coincident with the center $\hat{C}$ of the boundary. Since the virtual center of rotation $\hat{Q}$ is also assumed to be coincident with $\hat{C}$ then the principal point is stationary across frames i, independently of the rotation of the lens with respect to camera-head. In this case, and considering the interdependence between focal length, distortion, image diameter and FoV expressed by $\Phi$, the focal length $\hat{f}$ that grants the specified FoV of $\hat{\Theta}$ is the solution of $\Phi(\hat{f}, \hat{\xi}, \hat{\Theta}/2, \hat{d}/2)=0$.

Figure 10:
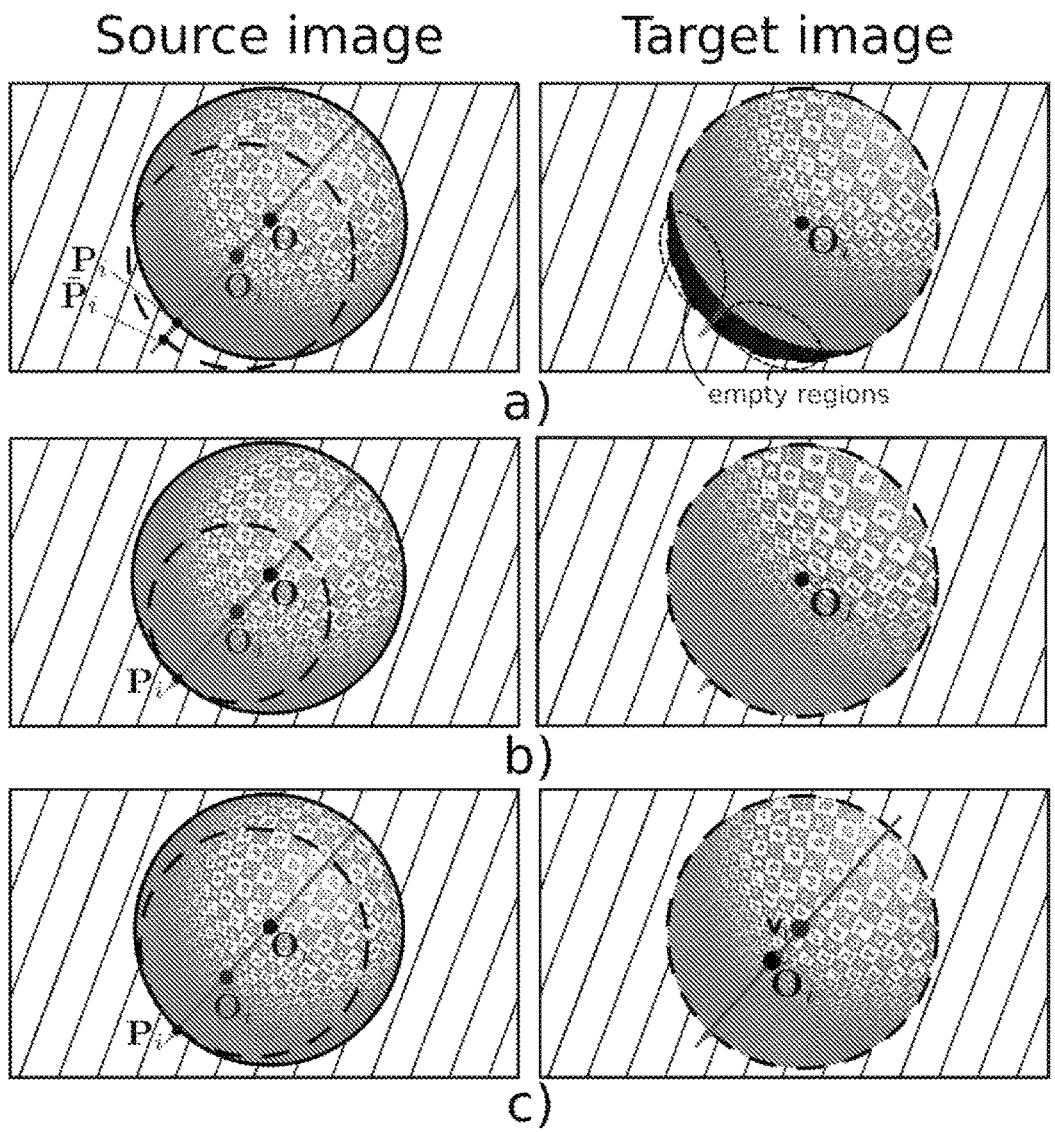
FIG. 10 shows the strategies to prevent the images rendered by the target camera from having regions without visual content (empty regions).

The problem of this choice of $\hat{f}$ and $\hat{O}_i$ is that the rendered target image often has a region without visual content (the empty region) near the intersection of $n_i$ with the boundary (FIG. 10 (a) RIGHT). This happens whenever angle $\Psi_i$, the limit viewing angle, defined by the back-projection rays of $\overline{O}_i$ and its closest point in the boundary of the source image $\overline{S}_i$, is smaller than half of the desired FoV $\hat{\Theta}$.

The empty region arises whenever the selected warping function w maps the target image beyond the boundary of the source image where there are no visual contents (FIG. 10(a) LEFT). This is obviously an undesirable artifact that undermines the user experience in varying the DoV via software.

Setting B: A possible solution to avoid the empty region artifact is to relax the FoV requirement and make it twice the limiting viewing angle $\Psi_i$ (FIG. 10 (b) RIGHT). In this case, the principal point is still kept in the center of the boundary ($\hat{O}_i=\hat{C}$) and $\hat{f}$ is determined by solving $\Phi(\hat{f}, \hat{\xi}, \Psi_i, \hat{d}/2)=0$ with respect to $\hat{f}$. Setting B has the drawback that the FoV of the target image can be substantially smaller than what was specified, which is in general an issue in terms of application (FIG. 10(b) LEFT).

Setting C: This disclosure discloses an alternative method to choose the focal length and principal point of the target image that conciliates the change in inclination of the DoV by an angle $\gamma$, with the rendering of an image with the desired FoV $\hat{\Theta}$ and no empty regions (FIG. 10(c) RIGHT). The different steps that comprise this novel method are provided in the scheme of FIG. 11. The strategy serves to compensate the lack of visual contents in the top or bottom of the source image by the visual contents that are available below or above, in case $\gamma<0$ or $\gamma>0$, respectively.

For illustrative purposes let the shift in the DoV be a positive angular offset $\gamma>0$ (FIG. 10(c) LEFT) such that the limiting viewing angle $\Psi_i$ is measured towards the notch (the down direction). Since the FoV of the target image in the down direction has to be decreased by an amount $\hat{\Theta}-\Psi_i$ to avoid the creation of an empty region, the idea is to increase the FoV in the up direction by the same amount to obtain an overall FoV of $\hat{\Theta}$ as in the specified requirements for the target camera. The shift of FoV from down to up directions causes the principal point to shift downwards by an amount $\lambda$, such that $\hat{O}_i=\hat{C}+\lambda v_i$. In this case, the focal length $\hat{f}$ and $\lambda$ can be determined by solving the following system of equations $$\begin{cases} \Phi(\hat{f}, \hat{\xi}, \Psi_i, \hat{d}/2 - \lambda) = 0 \\ \Phi(\hat{f}, \hat{\xi}, \hat{\Theta} - \Psi_i, \hat{d}/2 + \lambda) = 0 \end{cases}.$$

Note that if $\gamma<0$, the shift in the FoV is from up to down directions and the principal point translates upwards, i.e., $\hat{O}_i=\hat{C}-\lambda v_i$.

If $\Theta \geq \hat{\Theta}$, with $\Theta$ being the FoV of the source camera, then the disclosed method for selecting $\hat{f}$ and $\hat{O}_i$ always succeeds in rendering a target image with the desired FoV and no empty region. Conciliating these two features is important to provide a good user experience, but there are situations in which this is accomplished by significantly deviating the principal point towards the periphery of the target image. This might be undesirable for certain applications, specially the ones where the target camera is intended to mimic a particular real endoscopic camera, in which case the principal point is typically close to the image the center.

Applications and Functionalities

The disclosed image processing methods for changing the DoV of endoscopic systems with exchangeable, rotatable optics can lead to multiple applications and be employed in several different systems. The disclosure describes some embodiments of these systems and applications, without prejudice of other possible applications.

Electronic Switch Between Rigid Endoscopes with Different Lens Cut β

Manufacturers of rigid endoscopes provide lenses with different angular offsets from the mechanical axis with the most common lens cuts being $\beta=0°$, $30°$, $45°$, $70°$. Although surgical procedures usually favor endoscopes with a particular cut angle, there are moments or steps in the surgery where a different lens cut would be more convenient. For example, in knee arthroscopy the preference goes for arthroscopes with 30° lens cut, but the meniscus inspection in anterior or intercondylar regions benefits from a cut angle of 0° or 70°.

The problem is that, since a lateral change in DoV requires to physically switch the endoscope, which causes disruption and can involve risks for the patient, the surgeons rarely do it in practice and perform the procedure with the same endoscope, even when the visualization is sub-optimal.

The disclosed method can be used in a system to process the images and video acquired by an endoscopy camera equipped with a lens with a wide FoV to empower the surgeon with electronic switch between two or more virtual endoscopes with different lens cuts β. Such system overcomes the above-mentioned difficulty, that precludes the surgeon from having the best possible visualization at every surgical moment or step.

Figure 11:
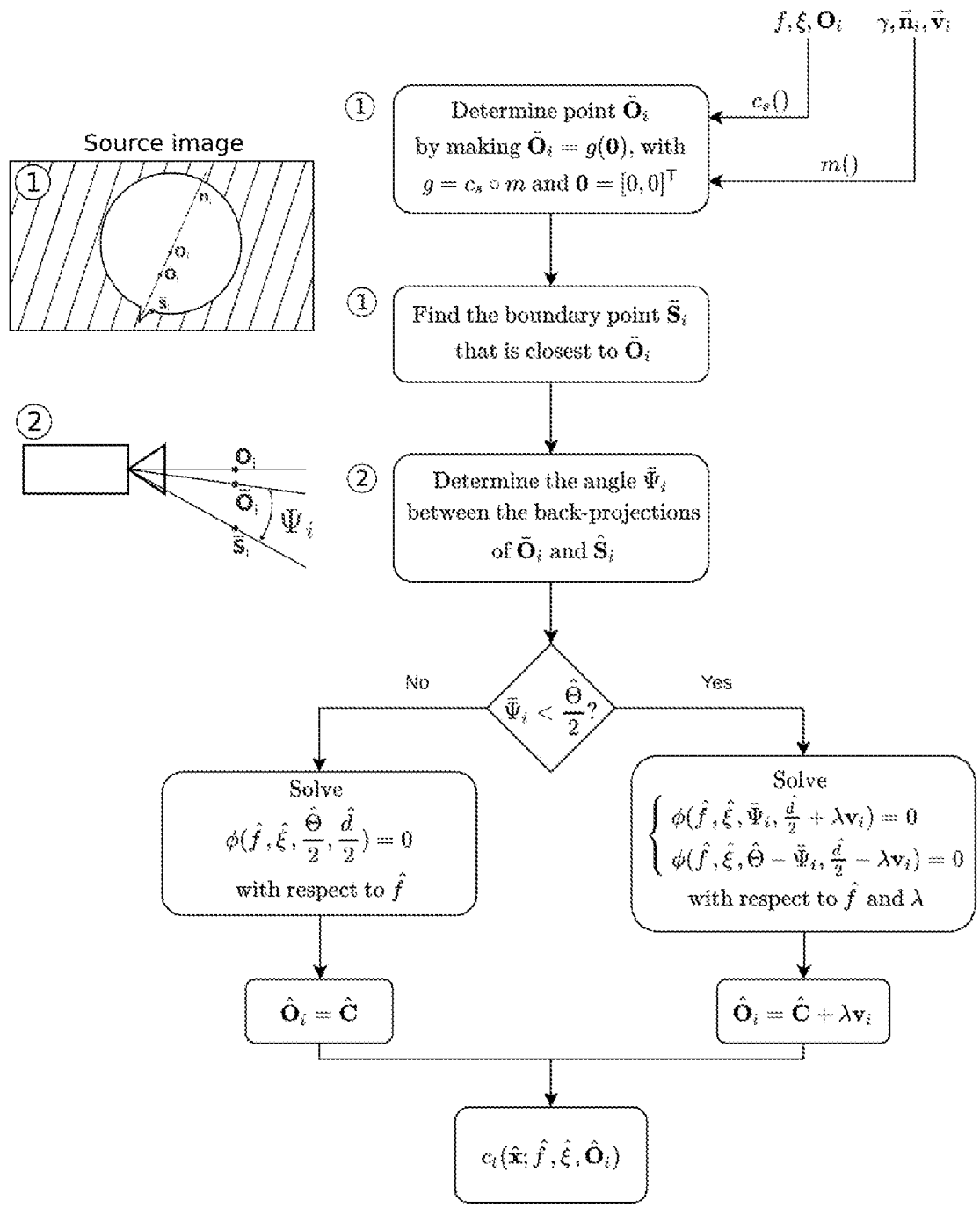
FIG. 11 describes the different steps of the method in this disclosure for estimating the focal length and principal point of the target image that conciliate the change in the DoV with the rendering of an image with the desired FoV and no empty regions.
Figure 12:
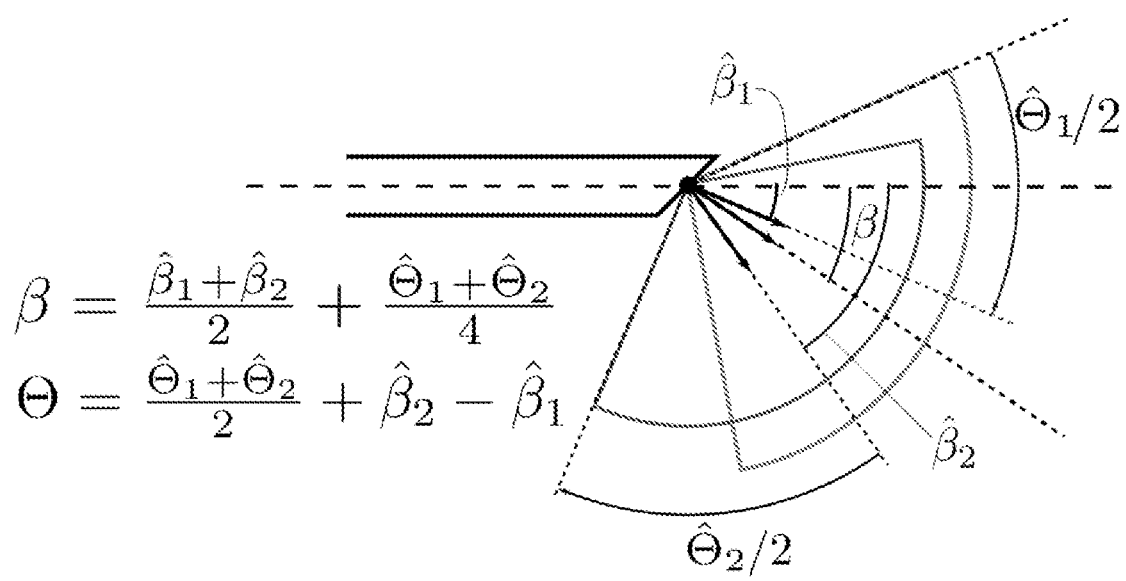
FIG. 12 shows how to dimension a source camera such that it properly accommodates the lens cuts and FoVs of targeted cameras by rendering realistic target images without empty regions and having the principal point close to the image center.

Let the two desired virtual endoscopes have lens cuts $\hat{\beta}_1$ and $\hat{\beta}_2$ and FoVs $\hat{\Theta}_1$ and $\hat{\Theta}_2$, respectively. Although the disclosed method for selecting the focal length and principal point (FIG. 10 (c) and FIG. 11) delivers the desired FoV for most settings of source camera, it might happen that the principal point deviates too much from the center of the target image, which diminishes the user experience in terms of realistic virtualization of endoscopes with different lens cuts. The strategy to prevent this issue is to have a source camera with a lens cut β and FoV Θ that can properly accommodate the lens cuts and FoVs of the targeted cameras. As shown in FIG. 12, and given the specifications $\hat{\beta}_1$, $\hat{\Theta}_1$ and $\hat{\beta}_2$, $\hat{\Theta}_2$ of the two target cameras, this is accomplished if β and Θ are approximately $$\beta = \frac{\hat{\beta}_1 + \hat{\beta}_2}{2} + \frac{\hat{\Theta}_1 - \hat{\Theta}_2}{4} \text{ and } \Theta = \frac{\hat{\Theta}_1 + \hat{\Theta}_2}{2} + \hat{\beta}_2 - \hat{\beta}_1.$$

Figure 13:
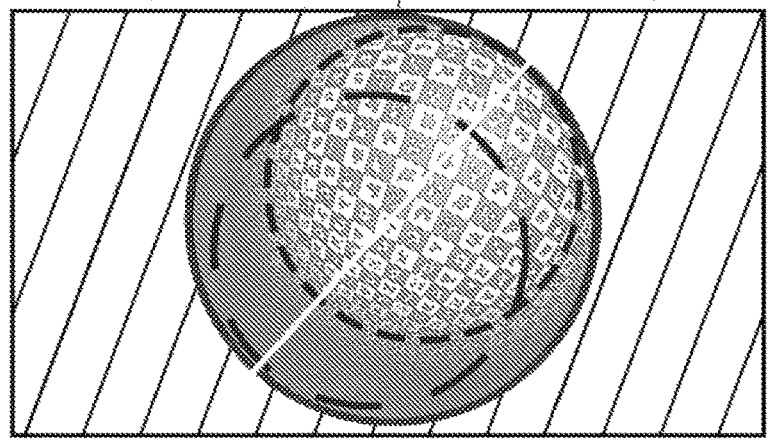
FIG. 13 shows the image results of rendering two images acquired with two endoscopes with different lens cuts and FoVs. The top figure shows the image acquired by the real camera, which is a laparoscope with a lens cut $\beta=45°$ and a diameter of 10 mm. The middle figure shows the virtual view obtained for $\gamma_1=-15°$, in which case an endoscope with lens cut $\hat{\beta}_1=30°$ and FoV $\hat{\Theta}_1=60°$ is virtualized. The bottom figure depicts the virtual view obtained for $\gamma_2=25°$ which means that the endoscopic camera is looking downwards with respect to the symmetry axis of the scope, having $\hat{\beta}_2=70°$ and FoV $\hat{\Theta}_2=50°$.
Figure 13:
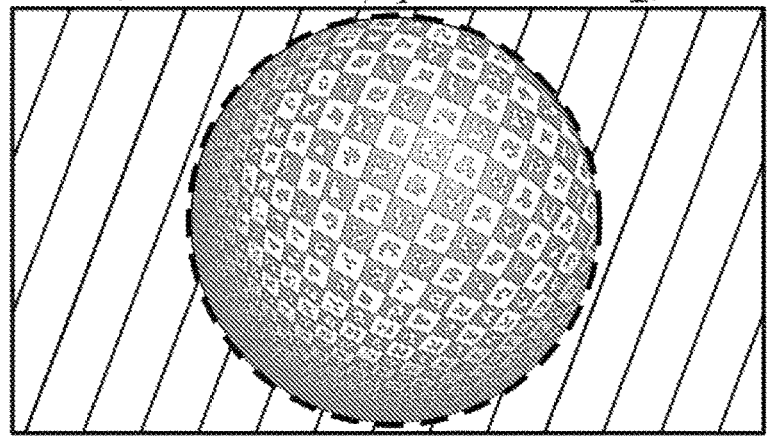
Figure 13:
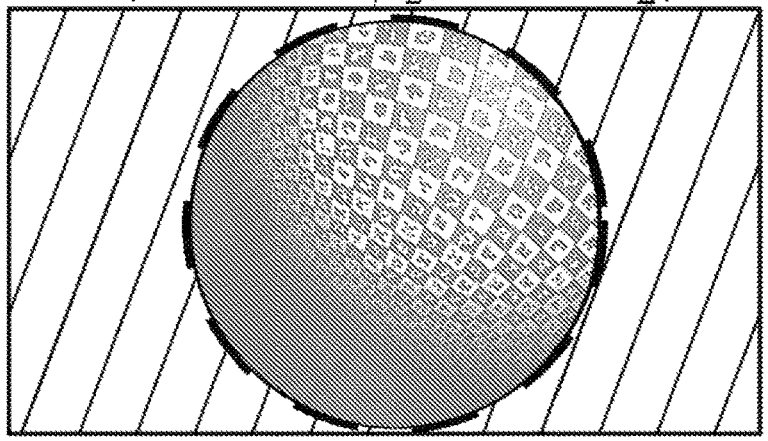

An embodiment is to use the disclosed methods in a system to electronically switch between the two most common cut angles used in arthroscopy. Since a standard 30° arthroscope has $\hat{\beta}_1=30°$, $\hat{\Theta}_1=110°$ and a 70° arthroscope has $\hat{\beta}_2=70°$, $\hat{\Theta}_2=90°$, then it stems from the calculations above that the ideal source camera should have a cut angle β around 45° and FoV Θ of approximately 140°. These values are merely indicative and serve to assure the rendering of realistic target images with the principal point in the center region. Let f, ξ, $O_i$ be the exact calibration of the source camera, and let $\hat{d}_1$, $\hat{d}_2$ and $\hat{\xi}_1$, $\hat{\xi}_2$ be, respectively, the image diameters and distortions that complement the specifications for the two target cameras, and that can be either arbitrary or obtained from the calibration of real lenses. The method of FIG. 8 is used to process the images acquired by the real source camera where a user command switches the settings of the target camera to alternate between the 30° lens (target 1) and the 70° lens (target 2) (FIG. 13).

Electronic Change of DoV, Distortion Correction and Directional Zoom

So far the method of FIG. 8 has been used to select a part of the FoV of the source camera and mimic the video output that would be acquired by a camera with smaller FoV and different lens cut placed in the same 3D location.

Figure 14:
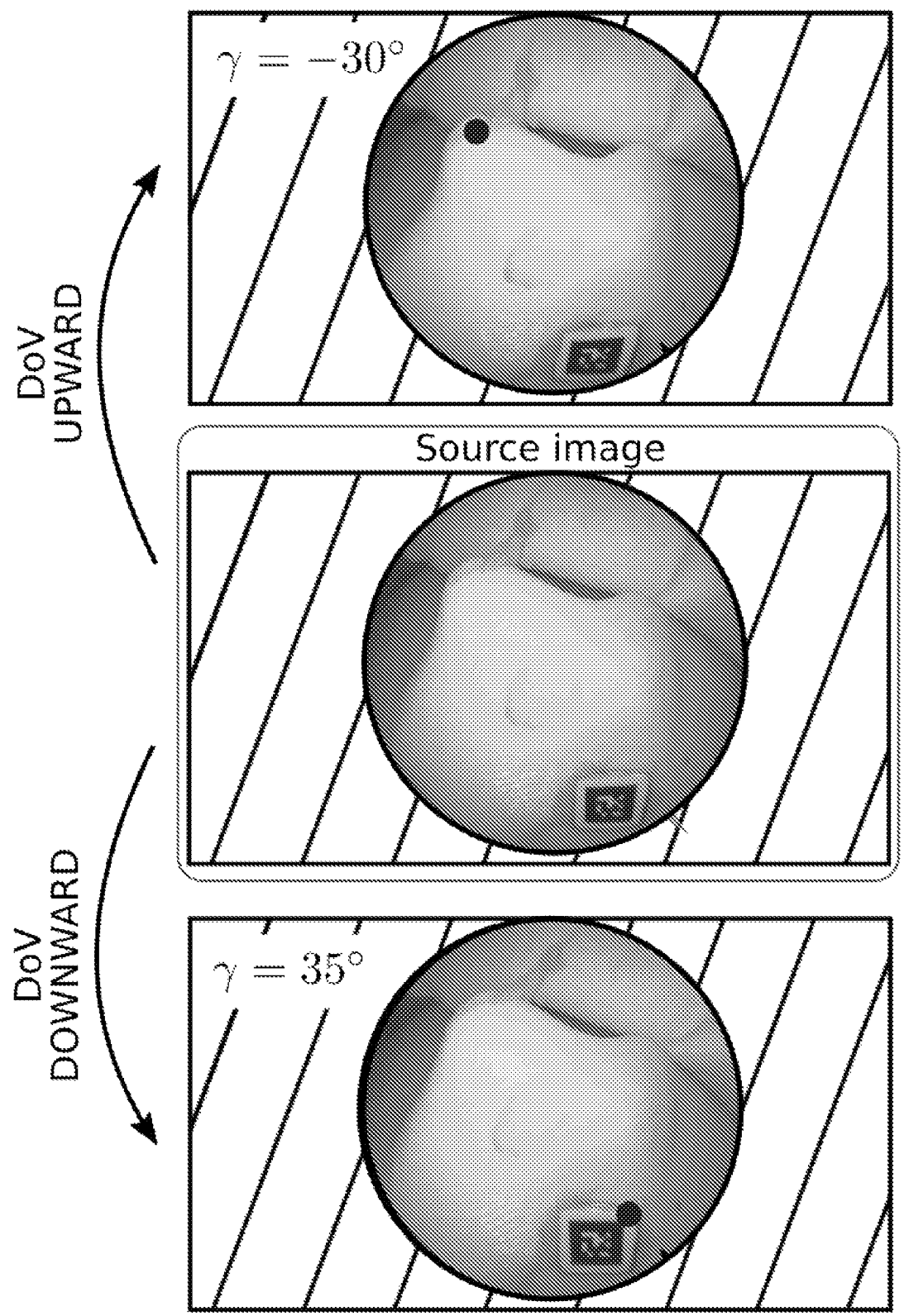
FIG. 14 shows the image results of changing the DoV by an angle $\gamma$ while predefining the parameters of the target camera to be the same as the calibration estimates of the source camera. The top figure is the original, real image acquired by an arthroscope with a lens cut $\beta=30°$. The middle figure shows the virtual view obtained for $\gamma=-30°$, in which case the arthroscope is forward viewing along its symmetry axis ($\beta+\gamma=0°$). The bottom figure depicts the virtual view obtained for $\gamma=35°$ which means that the camera is looking downwards $\beta+\gamma=65°$ with respect to the symmetry axis of the scope. The filled circles indicate the location of $\overline{O}_i$, which is the point in the source image where the principal point of the target image is mapped, showing that a change in the DoV causes a shift in the principal point.

Another possible embodiment or application is to use the disclosed method to shift the DoV of a particular endoscopic camera while maintaining the overall FoV, in which case the principal point in the rendered images moves towards the periphery as the shift in DoV increases (FIG. 14). In this case the disclosed methods of FIG. 8 and FIG. 11 are executed in a system that is connected to the source camera, where the distortion $\hat{\xi}$, image diameter $\hat{d}$, and FoV $\hat{\Theta}$ of the target camera are set with the same values as the source camera, and where the angular shift γ in the DoV is commanded by the user that can freely move it both upwards or downwards (FIG. 14).

The system that is described can be further enhanced with the possibility of user controlled distortion, in which case the setting $\hat{\xi}=0$, γ=0 will cause the system to correct the radial distortion in the source video.

Figure 15:
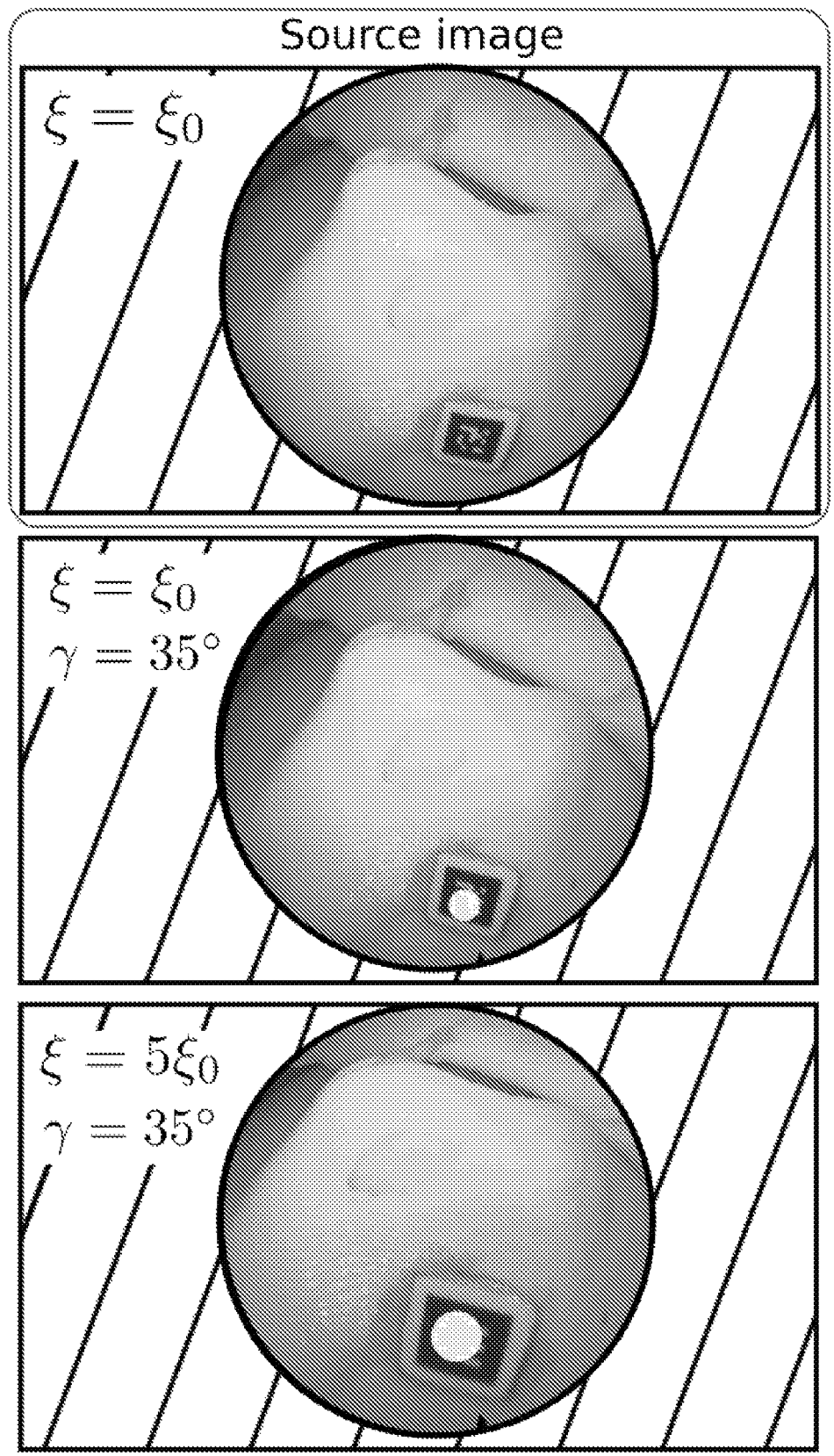
FIG. 15 shows the image results for the directional zoom that enables to scale up the image around an arbitrary viewing direction while preserving the overall FoV and image contents. The top figure shows the original view. The middle figure shows the rendering results for $\beta=65°$ for the case of the pre-sets of the target camera being the calibration of the source camera. The bottom figure shows the virtual view for the case of the radial distortion being $\hat{\xi}=5 \xi$ while the lens cut is the same as in middle figure. It can be observed that by increasing the radial distortion it is possible to zoom in the region of interest while preserving all image contents that appear in the top figure. The filled circles indicate the location of $\overline{O}_i$, which is the point in the source image where the principal point of the target image is mapped, showing that a change in the DoV causes a shift in the principal point.

The disclosed system can also be used to implement what is referred to as directional zoom, in which case the angular shift γ is adjusted such that the principal point in the rendered image becomes overlaid with a region of interest (ROI) and the distortion $\hat{\xi}$ is increased to magnify the ROI while maintaining the FoV and all visual contents in the image (FIG. 15). As an alternative, the magnification of the ROI can also be accomplished by maintaining the distortion and increasing the focal length $\hat{f}$ in which case the FoV decreases and some image contents will be lost.

Other Applications

The disclosed methods of the schemes of FIG. 8 and FIG. 11 can be used to process a discrete set of images for the purpose of rendering images of virtual target cameras with different, known calibrations and/or lens cut angles to be used as input to train and/or test machine learning or deep learning based algorithms for automatic learning to identify and estimate different camera and/or lens characteristics, including, but not limited to, identification of the lens cut, estimation of the calibration parameters, learning to generate virtual images with different lens cuts.

The disclosed methods can also be applied to other types of imagery such as fundus images in ophthalmology.

The method that is disclosed for selecting the focal length and position of principal point in the target image (FIG. 11) is not limited to endoscopy applications and can be employed in the warping of generic images and video. One possible embodiment is the use of the method in systems of visual surveillance that implement electronic pan-and-tilt in images and videos acquired by a fish-eye camera.

Figure 16:
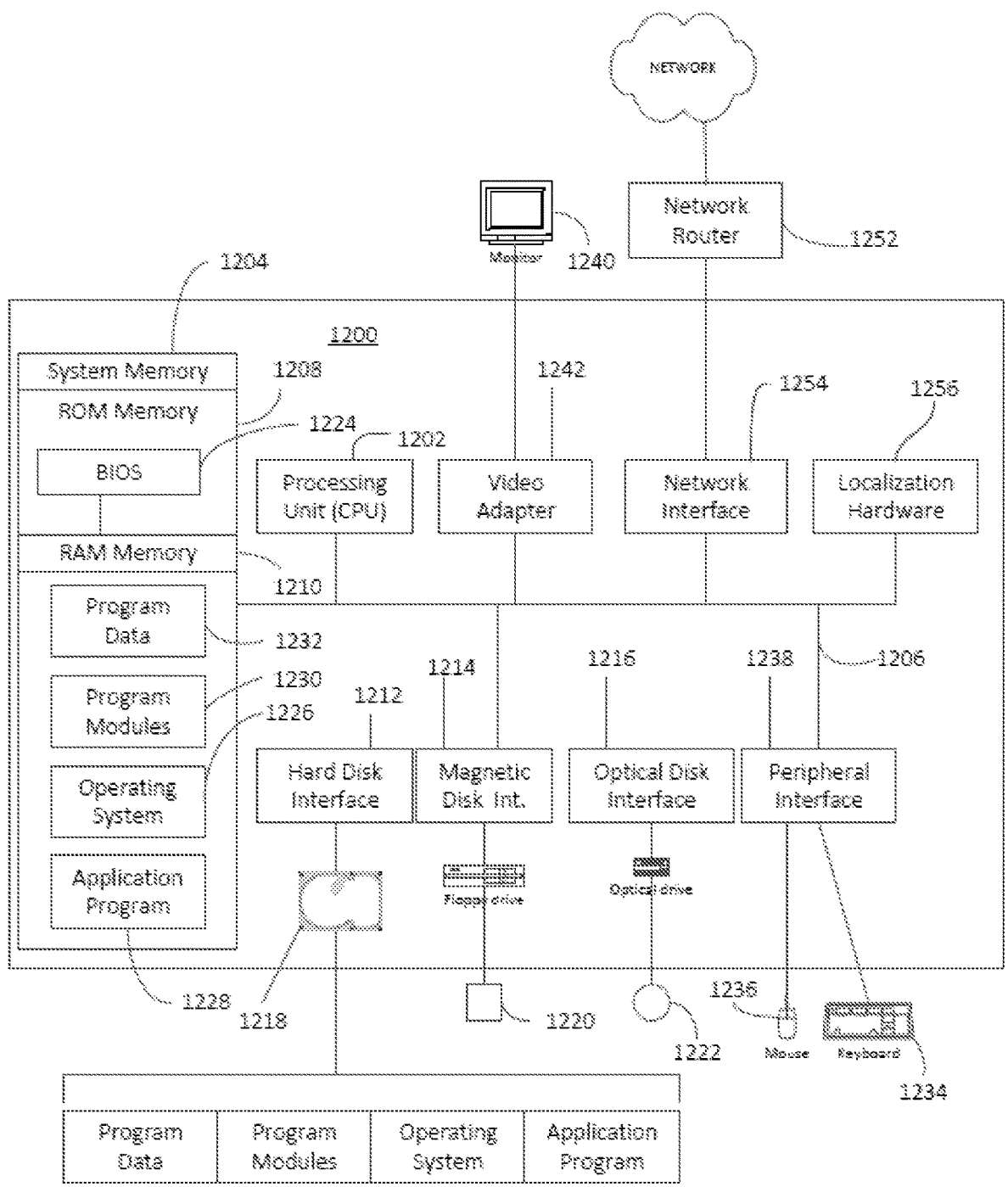
FIG. 16 is a diagrammatic view of an example computing system that includes a general purpose computing system environment.

FIG. 16 is a diagrammatic view of an illustrative computing system that includes a general purpose computing system environment 1200, such as a desktop computer, laptop, smartphone, tablet, or any other such device having the ability to execute instructions, such as those stored within a non-transient, computer-readable medium. Furthermore, while described and illustrated in the context of a single computing system 1200, those skilled in the art will also appreciate that the various tasks described hereinafter may be practiced in a distributed environment having multiple computing systems 1200 linked via a local or wide-area network in which the executable instructions may be associated with and/or executed by one or more of multiple computing systems 1200. Computing system environment 1200, or portions thereof, may find use for the processing, methods, and computing steps of this disclosure.

In its most basic configuration, computing system environment 1200 typically includes at least one processing unit 1202 and at least one memory 1204, which may be linked via a bus 1206. Depending on the exact configuration and type of computing system environment, memory 1204 may be volatile (such as RAM 1210), non-volatile (such as ROM 1208, flash memory, etc.) or some combination of the two. Computing system environment 1200 may have additional features and/or functionality. For example, computing system environment 1200 may also include additional storage (removable and/or non-removable) including, but not limited to, magnetic or optical disks, tape drives and/or flash drives. Such additional memory devices may be made accessible to the computing system environment 1200 by means of, for example, a hard disk drive interface 1212, a magnetic disk drive interface 1214, and/or an optical disk drive interface 1216. As will be understood, these devices, which would be linked to the system bus 1206, respectively, allow for reading from and writing to a hard disk 1218, reading from or writing to a removable magnetic disk 1220, and/or for reading from or writing to a removable optical disk 1222, such as a CD/DVD ROM or other optical media. The drive interfaces and their associated computer-readable media allow for the nonvolatile storage of computer readable instructions, data structures, program modules and other data for the computing system environment 1200. Those skilled in the art will further appreciate that other types of computer readable media that can store data may be used for this same purpose. Examples of such media devices include, but are not limited to, magnetic cassettes, flash memory cards, digital videodisks, Bernoulli cartridges, random access memories, nano-drives, memory sticks, other read/write and/or read-only memories and/or any other method or technology for storage of information such as computer readable instructions, data structures, program modules or other data. Any such computer storage media may be part of computing system environment 1200.

A number of program modules may be stored in one or more of the memory/media devices. For example, a basic input/output system (BIOS) 1224, containing the basic routines that help to transfer information between elements within the computing system environment 1200, such as during start-up, may be stored in ROM 1208. Similarly, RAM 1210, hard drive 1218, and/or peripheral memory devices may be used to store computer executable instructions comprising an operating system 1226, one or more applications programs 1228 (such as an application that performs the methods and processes of this disclosure), other program modules 1230, and/or program data 1232. Still further, computer-executable instructions may be downloaded to the computing environment 1200 as needed, for example, via a network connection.

An end-user, e.g., a customer, retail associate, and the like, may enter commands and information into the computing system environment 1200 through input devices such as a keyboard 1234 and/or a pointing device 1236. While not illustrated, other input devices may include a microphone, a joystick, a game pad, a scanner, etc. These and other input devices would typically be connected to the processing unit 1202 by means of a peripheral interface 1238 which, in turn, would be coupled to bus 1206. Input devices may be directly or indirectly connected to processor 1202 via interfaces such as, for example, a parallel port, game port, firewire, or a universal serial bus (USB). To view information from the computing system environment 1200, a monitor 1240 or other type of display device may also be connected to bus 1206 via an interface, such as via video adapter 1242. In addition to the monitor 1240, the computing system environment 1200 may also include other peripheral output devices, not shown, such as speakers and printers.

The computing system environment 1200 may also utilize logical connections to one or more computing system environments. Communications between the computing system environment 1200 and the remote computing system environment may be exchanged via a further processing device, such a network router 1252, that is responsible for network routing. Communications with the network router 1252 may be performed via a network interface component 1254. Thus, within such a networked environment, e.g., the Internet, World Wide Web, LAN, or other like type of wired or wireless network, it will be appreciated that program modules depicted relative to the computing system environment 1200, or portions thereof, may be stored in the memory storage device(s) of the computing system environment 1200.

The computing system environment 1200 may also include localization hardware 1256 for determining a location of the computing system environment 1200. In embodiments, the localization hardware 1256 may include, for example only, a GPS antenna, an RFID chip or reader, a Wi-Fi antenna, or other computing hardware that may be used to capture or transmit signals that may be used to determine the location of the computing system environment 1200.

In a first aspect of the instant disclosure, a method is disclosed that, given video acquired by a real source camera that comprises a camera-head and a rigid endoscope with lens cut $\beta$ that rotates in azimuth around a mechanical axis that intersects the image in a point Q, for which the focal length f, radial distortion $\xi$, and principal point O at a certain azimuth $\alpha_0$ are known, renders the video that would be acquired by a virtual target camera placed in the same 3D location as the source camera, but with a lens cut $\hat{\beta}$, Field-of-View $\hat{\Theta}$, and distortion $\hat{\xi}$, where each successive target image $\hat{I}_i$ with resolution of m×n and circular boundary of diameter $\hat{d}$ centered in point $\hat{C}$ is rendered by executing the following steps for each corresponding source image $I_i$: (i) finding the location of the principal point $O_1$ in the source image $I_i$ with azimuth $\alpha_i$ by rotating O around Q by an angular displacement in azimuth $\delta_i = \alpha_i - \alpha_0$; (ii) updating the camera model of the source camera that maps points x in the canonical image, which are the pinhole projection of points X in the 3D scene, into points u in the pixel image such that $u=c_s(x; f, O_i, \xi)$; (iii) determining the 3D location of a vertical plane $\Pi_i$ that contains, or passes close to, the mechanical axis and the optical axis of the source camera, by finding and back-projecting the line $n_i$ where $\Pi_i$ intersects the source image $I_i$; (iv) defining a 3D motion m between target and source cameras as the rotation by an angle $\gamma=\hat{\beta}-\beta$ around a direction $\vec{n}_i$ that is the normal of the vertical plane $\Pi_{i\ i}$, such that $x=m(\hat{x}; \gamma, \vec{n}_i)$, with $\hat{x}$ being a point in the canonical image of the target camera; (v) computing a focal length $\hat{f}$ and location of the principal point $\hat{O}_i$ for the target camera and deriving the corresponding camera model that maps points $\hat{x}$ into points $\hat{u}$ in the pixel image according to $\hat{u}=c_t(\hat{x}; \hat{f}, \hat{O}_i, \hat{\xi})$; and (vi) generating a target image $\hat{I}_i$ using image warping techniques where each pixel $\hat{u}$ in $\hat{I}_i$ is mapped into a point u in the source image $I_i$ by a mapping function w that is the composition of the functions $c_s$, m and the inverse of $c_t$ computed in step (v) ($w=c_s \cdot m \cdot c_t^{-1}$), such that the color value of $\hat{u}$ can be interpolated.

In an embodiment of the first aspect, the azimuth $\alpha_0$ is referenced by a particular notch position P, the source image $I_i$ is processed to detect the boundary with center $C_i$ and notch position $P_i$, the angular displacement in azimuth is estimated as $\delta_1 = \sphericalangle P_1QP_i$ and the line $n_i$ is defined by points $O_i$ and $P_i$.

In an embodiment of the first aspect, the method further comprises processing the rendered target image $\hat{I}_i$ to create a black frame such that meaningful image contents are within a circular region with center $\hat{C}$ and diameter $\hat{d}$ and to create a notch by placing a visual mark in point $\hat{P}_i=\hat{C}+\hat{d}/2\ v_i$ in the circular boundary, with $v_i$ being the 2D unit direction of image line $n_i$.

In an embodiment of the first aspect, the region that contains meaningful image contents can take any desired geometric shape, such as, but not limited to, a conic shape, a rectangular shape, an hexagonal shape or any other polygonal shape.

In an embodiment of the first aspect, point Q is determined on-the fly using the detection of points $P_i$ and/or $C_i$ in successive frames, in which case it does not have to be known or determined a priori.

In an embodiment of the first aspect, line $n_i$ is alternatively defined by points $O_1$ and Q or $O_i$ and $C_i$.

In an embodiment of the first aspect, the position of the principal point is given in a normalized reference frame attached to the circular boundary, in which case the computation of its pixel location $O_i$ at every frame time instant i can be accomplished without having to explicitly know the rotation center Q and angular displacement in azimuth $\delta_i$.

In an embodiment of the first aspect, the source camera is equipped with an optical encoder, or any other sensing device, that measures the rotation of the scope with respect to the camera-head and estimates the angular displacement in azimuth $\delta_i$ of step (i).

In an embodiment of the first aspect, the principal point O is coincident with the rotation center Q, in which case the camera model of the source camera does not have to be updated at every frame time instant as in step (ii).

In an embodiment of the first aspect, the distortion of the target camera $\hat{\xi}$ is set to zero in order for the rendered image $\hat{I}_i$ to be distortion free.

In an embodiment of the first aspect, the rendering of target image $\hat{I}_i$ in step (vi) is performed using any common method for image warping or pixel value interpolation including, but not limited to, interpolation by nearest neighbors, bilinear interpolation or bicubic interpolation.

In an embodiment of the first aspect, in step (v) the principal point is made coincident with the center of the boundary ($\hat{O}_i=\hat{C}$) and the focal length is chosen such that the FoV of the target camera is the desired $\hat{\Theta}$, in which case the value of $\hat{f}$ is obtained by solving $\Phi(\hat{f}, \hat{\xi}, \hat{\Theta}/2, \hat{d}/2)=0$, with $\Phi$ being the mathematical expression that relates focal length, radial distortion, image distance, and angle between back-projection rays, all of which are interdependent parameters.

In an embodiment of the first aspect, in step (v) the principal point is made coincident with the center of the boundary ($\hat{O}_i=\hat{C}$) and the focal length is chosen such that the rendered image never has a region without visual content (an empty region), the method comprising: finding a location $\overline{O}_i$ in the source image where the warping function will map the principal point $\hat{O}_i$, which can be determined by transforming the origin $[0, 0]^T$ by a function g that is the composition of the camera model $c_s$ and the motion m ($g=c_s \cdot m$); determining a limiting viewing angle $\Psi_i$ that is the angle between the back-projection rays of $\overline{O}_i$ and the point in the circular boundary closest to $\overline{O}_i$; if $\Psi_i<\hat{\Theta}/2$, reducing the camera FoV to $2\Psi_i$ and obtaining the value of $\hat{f}$ by solving the equation $\Phi(\hat{f}, \hat{\xi}, \Psi_i, \hat{d}/2)=0$, otherwise obtaining the value of $\hat{f}$ by solving the equation $\Phi(\hat{f}, \hat{\xi}, \hat{\Theta}/2, \hat{d}/2)=0$, with $\Phi$ being the mathematical expression that relates focal length, radial distortion, image distance, and angle between back-projection rays, all of which are interdependent parameters.

In an embodiment of the first aspect, in step (vi) the focal length $\hat{f}$ and principal point $\hat{O}_i$ are such that the rendered image has no empty region and the FoV of the target camera is the specified value $\hat{\Theta}$, the method comprising: finding a location $\overline{O}_i$ in the source image where the warping function will map the principal point $\hat{O}_i$, which can be determined by transforming the origin $[0, 0]^T$ Of by a function g that is the composition of the camera model $c_s$ and the motion m ($g=c_s \cdot m$); determining a limiting viewing angle $\Psi_i$ that is the angle between the back-projection rays of $\overline{O}_i$ and the point in the circular boundary closest to $\overline{O}_i$; if $\Psi_i<\hat{\Theta}/2$, solving the following system of equations with respect to the focal length $\hat{f}$ and $\lambda$:

$$\begin{cases} \Phi(\hat{f}, \hat{\xi}, \Psi_1, \hat{d}/2 - \lambda) = 0 \\ \Phi(\hat{f}, \hat{\xi}, \hat{\Theta} - \Psi_i, \hat{d}/2 + \lambda) = 0 \end{cases},$$

and obtaining the principal point as $\hat{O}_i=\hat{C}+\lambda v_i$, otherwise making $\hat{O}_i=\hat{C}$ and finding $\hat{f}$ by solving $\Phi(\hat{f}, \hat{\xi}, \hat{\Theta}/2, \hat{d}/2)=0$, with $\Phi$ being the mathematical expression that relates focal length, radial distortion, image distance, and angle between back-projection rays, all of which are interdependent parameters.

In an embodiment of the first aspect, the parameters of the target camera can be arbitrary, be predefined to accomplish a certain purpose, be equal to the calibration of a particular real camera equipped with a particular real endoscope with cut angle $\hat{\beta}$, be chosen by the user at the start of the procedure, or vary during operation according to particular events or user commands.

In an embodiment of the first aspect, the method is used in a system connected to a source camera for the purpose of empowering the user with the possibility of electronically switching between two virtual target cameras with lens cuts and FoVs of $\hat{\beta}_1$, $\hat{\Theta}_1$ and $\hat{\beta}_2$, $\hat{\Theta}_2$.

In an embodiment of the first aspect, the source camera is chosen such that the cut angle of the rigid endoscope is approximately $$\beta = \frac{\hat{\beta}_1 + \hat{\beta}_2}{2} + \frac{\hat{\Theta}_1 - \hat{\Theta}_2}{4}$$

and the FoV is approximately $$\Theta = \frac{\hat{\Theta}_1 + \hat{\Theta}_2}{2} + \hat{\beta}_2 - \hat{\beta}_1$$

to assure that the principal point in the target cameras is close to the center of the image.

In an embodiment of the first aspect, the FoV $\hat{\Theta}$, the distortion $\hat{\xi}$, the image resolution and the diameter $\hat{d}$ of the target camera are set with the same values as the source camera's and the cut angle $\hat{\beta}$ is set by the user that controls the amount of angular shift $\gamma$ that is added to the lens cut $\beta$ of the source camera such that $\hat{\beta}=\beta+\gamma$.

In an embodiment of the first aspect, both the distortion $\hat{\xi}$ and the angular shift $\gamma$ are set to zero, in which case the system will correct the radial distortion in the source image.

In an embodiment of the first aspect, the distortion $\hat{\xi}$ is set to zero for the target image to be rendered with no radial distortion independently of the chosen angular shift $\gamma$.

In an embodiment of the first aspect, the angular shift $\gamma$ is chosen such that the principal point is placed in a region of interest in the target image and the radial distortion parameter $\hat{\xi}$ is increased to magnify this region of interest while maintaining the FoV of the target camera and all contents visible.

In an embodiment of the first aspect, the source and/or target cameras have radial distortion described by any of the models known in the literature, including, but not limited to, learning-based models, Brown's polynomial model, the rational model, the fish-eye model, or the division model.

In an embodiment of the first aspect, the boundary with center $C_i$ and the notch $P_i$ are detected using a generic conic detection method, using machine learning or deep learning techniques, or any other image processing technique.

In an embodiment of the first aspect, multiple notch positions are detected and a particular notch of these multiple notches is used for determining the angular displacement in azimuth $\delta_i$ as the angle defined by points $P_i$, Q, P.

In an embodiment of the first aspect, the Field-of-View $\hat{\Theta}$ and the distortion $\hat{\xi}$ of the virtual target camera take the same values as the source camera's, but the lens cut $\hat{\beta}$ is set by the user at every frame time instant.

In an embodiment of the first aspect, the Field-of-View $\hat{\Theta}$ of the virtual target camera takes the same value as the source camera's, but the lens cut $\hat{\beta}$ and the distortion $\hat{\xi}$ is set by the user at every frame time instant.

In an embodiment of the first aspect, the Field-of-View $\hat{\Theta}$ and the lens cut $\hat{\beta}$ of the virtual target camera take the same values as the source camera's, but the distortion $\hat{\xi}$ is set by the user at every frame time instant to produce a zoom in or zoom out effect that does not change the FoV.

In an embodiment of the first aspect, the Field-of-View $\hat{\Theta}$ of the virtual target camera takes the same value as the source camera's, but the lens cut $\hat{\beta}$ and the distortion $\hat{\xi}$ are set by the user at every frame time instant to adapt the DoV and produce a zoom in or zoom out effect that does not change the FoV.

In an embodiment of the first aspect, the Field-of-View $\hat{\Theta}$ of the virtual target camera takes the same value as the source camera's, but the lens cut $\hat{\beta}$ and the focal length $\hat{f}$ are set by the user at every frame time instant, in which case the variable to solve for is not the focal length $\hat{f}$ but distortion $\hat{\xi}$ to produce a zoom in or zoom out effect that does not change the FoV.

While various embodiments have been described for purposes of this disclosure, such embodiments should not be deemed to limit the teaching of this disclosure to those embodiments. Various changes and modifications may be made to the elements and operations described above to obtain a result that remains within the scope of the systems and processes described in this disclosure. All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It will be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

The described embodiments are to be considered in all respects only as illustrative and not restrictive and the scope of the presently disclosed embodiments is, therefore, indicated by the appended claims rather than by the foregoing description. All changes which come within the meaning and range of equivalency of the claims are to be embraced within their scope. Skilled artisans may implement the described functionality in varying ways for each particular application, but such implementation decisions should not be interpreted as causing a departure from the scope of the disclosed systems and/or methods.

What is claimed is:

1. A method for rendering an image $\hat{I}_i$ of a virtual target camera based on a source image $I_i$ captured by a real source camera that is real, the source camera comprising a camera-head and a rigid endoscope with lens cut $\beta$ that rotates in azimuth around a mechanical axis that intersects the image in a point Q, for which the focal length f, radial distortion $\xi$, and principal point O at a certain azimuth $\alpha_0$ are known, the method comprising:

finding a location of the principal point $O_i$ in the source image $I_i$ with azimuth $\alpha_i$ by rotating O around Q by an angular displacement in azimuth $\delta_i = \alpha_i - \alpha_0$;

updating a camera model $c_s$ of the source camera that maps points x in a canonical image into points u in a pixel image according to the focal length f, radial distortion $\xi$, and location of the principal point $O_i$;

determining a 3D location of a vertical plane $\Pi_i$ that contains, or passes close to, the mechanical axis and an optical axis of the source camera, by finding and back-projecting a line $n_i$ where $\Pi_i$ intersects the source image $I_i$;

defining a 3D motion m between the target and source cameras as a rotation by an angle $\gamma = \hat{\beta} - \beta$ around a direction $\vec{n}_i$ that is normal to the vertical plane $\Pi_i$, such that $x = m(\hat{x}; \gamma, \vec{n}_i)$, with $\hat{x}$ being a point in the canonical image of the target camera;

computing a focal length $\hat{f}$ and a location of the principal point $\hat{O}_i$ for the target camera and deriving a camera model $c_t$ that maps points $\hat{x}$ in a canonical image of the target image into points $\hat{u}$ in a pixel image of the target image according to the focal length $\hat{f}$ and location of the principal point $\hat{O}_i$; and generating the target image $\hat{I}_i$ by mapping a plurality of pixels $\hat{u}$ in $\hat{I}_i$ into a point u in the source image $I_i$ with a mapping function w that is a composition of the camera model $c_s$ of the source camera, the 3D motion m, and an inverse of a camera model $c_t$ of the target camera.

2. The method of claim 1, wherein the azimuth $\alpha_0$ corresponds to a first notch position P, the method further comprising:

processing the source image $I_i$ to detect a boundary with a center $C_i$ and a second notch position $P_i$;

wherein rotating O around Q by an angular displacement in azimuth comprises estimating the angular displacement in azimuth according to the first notch position P, the second notch position $P_i$, and the point Q;

wherein the line $n_i$ is defined by points $O_i$ and $P_i$.

3. The method in claim 2, further comprising processing the rendered target image $\hat{I}_i$ to create a black frame defining an image region with center $\hat{C}$ and diameter $\hat{d}$ and to create a notch by placing a visual mark at point $\hat{P}_i = \hat{C} + \hat{d}/2 \, v_i$ in the circular boundary, with $v_i$ being the 2D unit direction of image line $n_i$.

4. The method of claim 3, wherein the image region comprises one or more of a circular shape, a conic shape, a rectangular shape, an hexagonal shape, or another polygonal shape.

5. The method of claim 2, wherein the source image $I_i$ comprises two or more source image frames, wherein point Q is determined by detecting one or more of point $P_i$ or point $C_i$ in successive ones of the two or more frames.

6. The method of claim 2, wherein processing the source image $I_i$ to detect a boundary with a center $C_i$ and a second notch position $P_i$ comprises detecting a plurality of second notch positions $P_j$, wherein one of the plurality of second notch positions is used for determining the angular displacement in azimuth $\delta_i$.

7. The method of claim 1, wherein the azimuth $\alpha_0$ corresponds to a first notch position P, the method further comprising:

processing the source image $I_i$ to detect a boundary with a center $C_i$ and a second notch position $P_i$;

wherein rotating O around Q by an angular displacement in azimuth comprises estimating the angular displacement in azimuth according to the first notch position P, the second notch position $P_i$, and the point Q;

wherein line $n_i$ is defined by:

points $O_i$ and Q; or points $O_i$ and $C_i$.

8. The method of claim 1, wherein the position of the principal point is given in a normalized reference frame disposed in or attached to the endoscope.

9. The method of claim 1, wherein the source camera is equipped with a sensor that measures the rotation of the endoscope with respect to the camera-head and estimates the angular displacement in azimuth $\delta_i$.

10. The method of claim 1, wherein the principal point O is coincident with the rotation center Q.

11. The method of claim 1, wherein a distortion of the target camera $\xi$ is set to zero.

12. The method of claim 1, wherein generating the target image $\hat{I}_i$ is performed using an image warping or pixel value interpolation comprising one or more of interpolation by nearest neighbors, bilinear interpolation, or bicubic interpolation.

13. The method of claim 1, wherein the principal point $\hat{O}_i$ is made coincident with a center $\hat{C}$ of a boundary of the virtual image and computing the focal length $\hat{f}$ comprises solving $\Phi(\hat{f}, \hat{\xi}, \hat{\Theta}/2, \hat{d}/2) = 0$, with $\Phi$ being a mathematical expression that relates focal length, radial distortion, image distance, and angle between back-projection rays.

14. The method of claim 1 wherein the principal point $\hat{O}_i$ is made coincident with a center $\hat{C}$ of a boundary of the virtual image, the method comprising:

transforming an origin $[0, 0]^T$ of the source image by a function g that is the composition of the camera model $c_s$ and the motion m to find a location $\overline{O}_j$ in the source image that maps to the principal point $\hat{O}_i$;

determining a limiting viewing angle $\Psi_i$ between the back-projection rays of $\overline{O}_i$ and a point in the circular boundary closest to $\overline{O}_i$;

when $\Psi_i < \hat{\Theta}/2$, reducing the camera field of view to $2\Psi_i$ and obtaining the value of $\hat{f}$ by solving the equation $\Phi(\hat{f}, \hat{\xi}, \Psi_i, \hat{d}/2) = 0$, with $\Phi$ being a mathematical expression that relates focal length, radial distortion, image distance, and angle between back-projection rays;

when $\Psi_i > \hat{\Theta}/2$, obtaining the value of $\hat{f}$ by solving the equation $\Phi(\hat{f}, \hat{\xi}, \hat{\Theta}/2, \hat{d}/2) = 0$, with $\Phi$ being a mathematical expression that relates focal length, radial distortion, image distance, and angle between back-projection rays, all of which are interdependent parameters.

15. The method of claim 1, further comprising:

transforming an origin $[0, 0]^T$ of the source image by a function g that is the composition of the camera model $c_s$ and the motion m to find a location $\overline{O}_j$ in the source image that maps to the principal point $\hat{O}_i$;

determining a limiting viewing angle $\Psi_i$ between the back-projection rays of $\overline{O}_i$ and a point in the circular boundary closest to $\overline{O}_i$;

when $\Psi_i < \hat{\Theta}/2$, solving the following system of equations with respect to the focal length $\hat{f}$ and $\lambda$:

$$\begin{cases} \Phi(\hat{f}, \hat{\xi}, \Psi_1, \hat{d}/2 - \lambda) = 0 \\ \Phi(\hat{f}, \hat{\xi}, \hat{\Theta} - \Psi_i, \hat{d}/2 + \lambda) = 0 \end{cases},$$

and obtaining the principal point as $\hat{O}_i = \hat{C} + \lambda v_i$;

when $\Psi_i > \hat{\Theta}/2$, setting $\hat{O}_i = \hat{C}$ and determining $\hat{f}$ by solving $\Phi(\hat{f}, \hat{\xi}, \hat{\Theta}/2, \hat{d}/2) = 0$, with $\Phi$ being the mathematical expression that relates focal length, radial distortion, image distance, and angle between back-projection rays, all of which are interdependent parameters.

16. The method of claim 15, wherein:

the source camera is chosen such that the cut angle of the rigid endoscope is approximately $$\beta = \frac{\hat{\beta}_1 + \hat{\beta}_2}{2} + \frac{\hat{\Theta}_1 - \hat{\Theta}_2}{4}$$

and the field of view is approximately $$\Theta = \frac{\hat{\Theta}_1 + \hat{\Theta}_2}{2} + \hat{\beta}_2 - \hat{\beta}_1,$$

wherein $\hat{\beta}_1$ and $\hat{\Theta}_1$ are the lens cut and field of view, respectively, of a first virtual target camera and $\hat{\beta}_2$ and $\hat{\Theta}_2$ are the lens cut and field of view, respectively, of a second virtual target camera, wherein the virtual target camera is the first virtual target camera or the second virtual target camera.

17. The method of claim 15, wherein the $\hat{\Theta}$, the distortion $\hat{\xi}$, the image resolution, and the diameter $\hat{d}$ of the target camera are set with the same respective values as the source camera's and a cut angle $\hat{\beta}$ of the target camera is set by a user through user selection of an amount of angular shift $\gamma$ that is added to the lens cut $\beta$ of the source camera.

18. The method of claim 17, wherein the distortion $\hat{\xi}$ is zero.

19. The method of claim 18, wherein the angular shift $\gamma$ is zero.

20. The method of claim 15, wherein a cut angle $\hat{\beta}$ of the target camera is set by a user through user selection of an amount of angular shift $\gamma$ that is added to the lens cut $\beta$ of the source camera, wherein the angular shift $\gamma$ is chosen by the user such that the principal point is placed in a region of interest in the target image and the radial distortion parameter $\hat{\xi}$ is increased relative to the radial distortion $\xi$ of the source camera to magnify the region of interest.

21. The method of claim 1, wherein a field of view $\hat{\Theta}$ of the virtual target camera and the distortion $\hat{\xi}$ of the virtual target camera take the same values as the source camera's, and a lens cut $\hat{\beta}$ of the virtual target camera is set by a user.

22. The method of claim 1 wherein a field of view $\hat{\Theta}$ of the virtual target camera takes the same value as the source camera's, and the lens cut $\hat{\beta}$ of the virtual target camera and the distortion $\hat{\xi}$ of the virtual target camera are set by a user.

23. The method of claim 22, wherein the lens cut $\hat{\beta}$ and the distortion $\hat{\xi}$ are set by the user to adapt the depth of view and produce a zoom effect that does not change the field of view.

24. The method of claim 1 wherein the field of view $\hat{\Theta}$ and the lens cut $\hat{\beta}$ of the virtual target camera take the same values as the source camera's, and the distortion $\hat{\xi}$ of the virtual target camera is set by a user.

25. The method of claim 1 wherein field of view $\hat{\Theta}$ of the virtual target camera takes the same value as the source camera's, and a lens cut $\hat{\beta}$ and the focal length $\hat{f}$ of the virtual target camera are set by the user.

26. The method of claim 25, wherein the principal point $\hat{O}_i$ is made coincident with a center $\hat{C}$ of a boundary of the virtual image and computing the distortion $\hat{\xi}$ comprises solving $\Phi(\hat{f}, \hat{\xi}, \hat{\Theta}/2, \hat{d}/2)=0$, with $\Phi$ being a mathematical expression that relates focal length, radial distortion, image distance, and angle between back-projection rays.

27. The method of claim 25, wherein the principal point $\hat{O}_i$ is made coincident with a center $\hat{C}$ of a boundary of the virtual image, the method comprising:
transforming an origin $[0, 0]^T$ of the source image by a function g that is the composition of the camera model $c_s$ and the motion m to find a location $\overline{O}_i$ in the source image that maps to the principal point $\hat{O}_i$;
determining a limiting viewing angle $\Psi_i$ between the back-projection rays of $\overline{O}_i$ and a point in the circular boundary closest to $\overline{O}_i$;
when $\Psi_i < \hat{\Theta}/2$, reducing the camera field of view to $2\Psi_i$ and obtaining the value of distortion $\hat{\xi}$ by solving the equation $\Phi(\hat{f}, \hat{\xi}, \Psi_i, \hat{d}/2)=0$, with $\Phi$ being a mathematical expression that relates focal length, radial distortion, image distance, and angle between back-projection rays;
when $\Psi_i > \hat{\Theta}/2$, obtaining the value of distortion $\hat{\xi}$ by solving the equation $\Phi(\hat{f}, \hat{\xi}, \hat{\Theta}/2, \hat{d}/2)=0$, with $\Phi$ being a mathematical expression that relates focal length, radial distortion, image distance, and angle between back-projection rays, all of which are interdependent parameters.

28. The method of claim 25, further comprising:
transforming an origin $[0, 0]^T$ of the source image by a function g that is the composition of the camera model $c_s$ and the motion m to find a location $\overline{O}_i$ in the source image that maps to the principal point $\hat{O}_i$;
determining a limiting viewing angle $\Psi_i$ between the back-projection rays of $\overline{O}_i$ and a point in the circular boundary closest to $\overline{O}_i$;
when $\Psi_i < \hat{\Theta}/2$, solving the following system of equations with respect to the distortion $\hat{\xi}$ and $\lambda$:

$$\begin{cases} \Phi(\hat{f}, \hat{\xi}, \Psi_1, \hat{d}/2 - \lambda) = 0 \\ \Phi(\hat{f}, \hat{\xi}, \hat{\Theta} - \Psi_i, \hat{d}/2 + \lambda) = 0 \end{cases},$$

and obtaining the principal point as $\hat{O}_i = \hat{C} + \lambda v_i$;
when $\Psi_i > \hat{\Theta}/2$, setting $\hat{O}_i = \hat{C}$ and determining distortion $\hat{\xi}$ by solving $\Phi(\hat{f}, \hat{\xi}, \hat{\Theta}/2, \hat{d}/2)=0$, with $\Phi$ being the mathematical expression that relates focal length, radial distortion, image distance, and angle between back-projection rays, all of which are interdependent parameters.

29. A system for rendering an image $\hat{I}_i$ of a virtual target camera based on a source image $I_i$ captured by a source camera that is real, the source camera comprising a camera-head and a rigid endoscope with lens cut $\beta$ that rotates in azimuth around a mechanical axis that intersects the image in a point Q, for which the focal length f, radial distortion $\xi$, and principal point O at a certain azimuth $\alpha_0$ are known, the system comprising:
a non-transitory computer-readable medium storing instructions; and
a processor configured to execute the instructions to perform a method comprising:
finding a location of the principal point $O_i$ in the source image $I_i$ with azimuth $\alpha_i$ by rotating O around Q by an angular displacement in azimuth $\delta_i = \alpha_i - \alpha_0$;
updating a camera model $c_s$ of the source camera that maps points x in a canonical image into points u in a pixel image according to the focal length f, radial distortion $\xi$, and location of the principal point $O_i$;
determining a 3D location of a vertical plane $\Pi_i$ that contains, or passes close to, the mechanical axis and an optical axis of the source camera, by finding and back-projecting a line $n_i$ where $\Pi_i$ intersects the source image $I_i$;
defining a 3D motion m between the target and source cameras as a rotation by an angle $\gamma = \hat{\beta} - \beta$ around a direction $\vec{n}_i$ that is normal to the vertical plane $\Pi_{i,i}$, such that $x = m(\hat{x}; \gamma, \vec{n}_i)$, with $\hat{x}$ being a point in the canonical image of the target camera;
computing a focal length $\hat{f}$ and a location of the principal point $\hat{O}_i$ for the target camera and deriving a camera model that maps points $\hat{x}$ into points $\hat{u}$ in the pixel image according to the focal length $\hat{f}$ and location of the principal point $\hat{O}_i$; and
generating the target image $\hat{I}_i$ by mapping a plurality of pixels $\hat{u}$ in $\hat{I}_i$ into a point u in the source image $I_i$ with a mapping function w that is a composition of the camera model $c_s$ of the source camera, the 3D motion m, and an inverse of a camera model $c_t$ of the target camera, wherein the camera model $c_t$ of the target camera maps points in a canonical image of the target camera into points in a pixel image of the target camera.

30. A method for rendering a virtual image $\hat{I}_i$ of a virtual target camera, the method comprising:

obtaining a source image $I_i$ captured by a source camera that is real, the source camera comprising a medical scope;

finding a location of a principal point $O_i$ in the source image $I_i$ with azimuth $\alpha_i$, wherein the real source camera is associated with a camera model $c_s$ that maps points x in a canonical image into points u in a pixel image according to the location of the principal point $O_i$;

determining a 3D location of a vertical plane $\Pi_i$ proximate a mechanical axis and an optical axis of the source camera, by finding and back-projecting a line $n_i$ where $\Pi_i$ intersects the source image $I_i$;

defining a 3D motion m between the target and source cameras as a rotation around a direction $\vec{n}_i$ that is normal to the vertical plane $\Pi_i$;

deriving a camera model $c_t$ that maps points $\hat{x}$ in a canonical image of the virtual image $\hat{I}_i$ into points $\hat{u}$ in a pixel image of the virtual image $\hat{I}_i$; and generating the target image $\hat{I}_i$ by mapping a plurality of pixels $\hat{u}$ in $\hat{I}_i$ into a point u in the source image $I_i$ with a mapping function w that is a composition of the camera model $c_s$ of the source camera, the 3D motion m, and an inverse of a camera model $c_t$ of the target camera.

\* \* \* \* \*